United States Patent
Buhlmann et al.

(10) Patent No.: US 8,765,060 B2
(45) Date of Patent: Jul. 1, 2014

(54) CHEMICAL SENSOR

(75) Inventors: Philippe Buhlmann, Minneapolis, MN (US); Paul G. Boswell, Arden Hills, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1374 days.

(21) Appl. No.: 11/915,551

(22) PCT Filed: May 26, 2006

(86) PCT No.: PCT/US2006/020366
§ 371 (c)(1),
(2), (4) Date: Jul. 28, 2008

(87) PCT Pub. No.: WO2006/127963
PCT Pub. Date: Nov. 30, 2006

(65) Prior Publication Data
US 2008/0293997 A1    Nov. 27, 2008

Related U.S. Application Data

(60) Provisional application No. 60/684,765, filed on May 26, 2005.

(51) Int. Cl.
*G01N 27/00* (2006.01)

(52) U.S. Cl.
USPC .......... 422/82.03; 422/82.01; 422/82.02; 422/83; 422/98; 436/68; 436/149

(58) Field of Classification Search
USPC .......... 422/82.01–82.08, 83, 98; 436/63, 68, 436/149, 164, 169, 172
See application file for complete search history.

(56) References Cited

U.S. PATENT DOCUMENTS

| | | | |
|---|---|---|---|
| 5,045,828 A | 9/1991 | Kulwicki et al. | |
| 5,110,645 A | 5/1992 | Matsumoto et al. | |
| 5,315,673 A | 5/1994 | Stetter et al. | |
| 5,453,248 A | 9/1995 | Olstein | |
| 5,591,407 A * | 1/1997 | Groger et al. | 422/82.05 |
| 5,650,483 A * | 7/1997 | Malik et al. | 528/402 |
| 5,681,532 A | 10/1997 | Kane et al. | |
| 6,103,033 A | 8/2000 | Say et al. | |
| 6,500,547 B1 * | 12/2002 | Potyrailo | 428/422 |
| 6,841,166 B1 | 1/2005 | Zhang et al. | |
| 2004/0101691 A1 | 5/2004 | White | |
| 2006/0034731 A1 * | 2/2006 | Lewis et al. | 422/88 |
| 2009/0125101 A1 * | 5/2009 | Zhao | 623/1.43 |

FOREIGN PATENT DOCUMENTS

| | | |
|---|---|---|
| EP | 0 345 052 B1 | 3/1993 |
| WO | WO 02/11225 A1 | 2/2002 |
| WO | WO 03/052406 A1 | 6/2003 |

OTHER PUBLICATIONS

PCT International Search Report; International App. No. PCT/US06/20366; Oct. 31, 2006.

Bühlmann, Philippe et al., Carrier-Based Ion-Selective Electrodes and Bulk Optodes. 2. Ionophores for Potentiometric and Optical Sensors, *Chem. Rev.*, 98, 1593-1687, 1998.

(Continued)

*Primary Examiner* — Jill Warden
*Assistant Examiner* — Dwayne K Handy
(74) *Attorney, Agent, or Firm* — Viksnins Harris & Padys PLLP

(57) ABSTRACT

A device for detecting an analyte present in a fluid includes a fluorous sensing phase into which the analyte enters selectively in comparison with other components of the fluid.

49 Claims, 15 Drawing Sheets

(56) References Cited

OTHER PUBLICATIONS

Frost, Megan C. et al., "Controlled Photoinitiated Release of Nitric Oxide from Plymer Films Containing S-Nitroso-*N*-acetyl-DL-penicillamine Derivatized Fumed Silica Filler", *J. Am. Chem. Soc.*, 126, 1348-1349, 2004.

Wisniewski, Natalie et al, "Methods for reducing biosensor membrane biofouling", *Colloids and Surfaces B: Biointerfaces*, 18, 197-219, 2000.

Bakker, Eric et al., "Carrier-Based Ion-Selective Electrodes and Bulk Optodes. 1. General Characteristics", *Chem. Rev.*, 97, 3083-3132, 1997.

Boswell, Paul G. et al., "Fluorous Bulk Membranes for Potentiometric Sensors with Wide Selectivity Ranges: Observation of Exceptionally Strong Ion Pair Formation", *J. Am. Chem. Soc.*, 127, 8958-8959, 2005.

Buhlmann, Philippe et al., "Influence of Natural, Electrically Neutral Lipids on the Potentiometric Responses of Cation-Selective Polymeric Membrane Electrodes", *Analytical Chemistry*, 73, 3199-3205, 2001.

Buhlmann, Philippe et al., "Perfluorinated Matrixes as New Materials for Receptor-Doped Chemical Sensors", *Book of Abstracts 229th ACS National Meeting*, 2005.

Kaul, N. et al., "HPTLC method for determination of nevirapine in pharmaceutical dosage form", *Talanta*, 62, 843-852, 2004.

Boswell P.G. et al., "Coordinative Properties of Highly Fluorinated Solvents with Amino and Ether Groups", *J. Am. Chem. Soc.* 127, pp. 16976-16984, 2005.

Johnson, R.D. et al., "Ionophore-based ion-selective potentiometric and optical sensors", *Analytical and Bioanalytical Chemistry*, 376, pp. 328-341, 2003.

Murphy, B. et al., "Study of the impact of penetrant characteristics upon diffusion into Teflon membranes to further assess the performance of an ATR/FTIR sensor", *Analytical and Bioanalytical Chemistry*, 377, pp. 195-202, 2003.

\* cited by examiner

Table 1

| ion | $Li^+$ | $Na^+$ | $Cs^+$ | $NH_4^+$ | $H_2O^+$ |
|---|---|---|---|---|---|
| $\log K_{ip}$ | 20.36±0.17 | 20.57±0.95 | 20.29±0.02 | 20.11±0.23 | 20.73±0.20 |

*Fig. 12*

Table 2

| membrane type | $\log K^{pol}_{C_{SJ}}$ (separate solution method) | | | | | |
|---|---|---|---|---|---|---|
| | $Ca^{2+}$ | $Li^+$ | $Na^+$ | $K^+$ | $N(Pr)_4^+$ | $N(Bu)_4^+$ |
| I (Fluorous, 2) | -4.35 | -4.01 | -3.75 | -2.59 | +9.08 | +11.41 |
| II (choroparaffin, KFPB) | -0.69 | -1.07 | -0.99 | -0.65 | +5.88 | +6.91 |
| III (oNPOE, 2) | -3.85 | -3.66 | -2.85 | -1.06 | +4.76 | +4.33 |
| IV (oNPOE, KClPB) | -3.79 | -3.66 | -2.90 | -1.07 | +5.48 | +4.41 |
| (ionophore[22a]) | -3.39 | -4.20 | -3.87 | -2.68 | | |
| (ionophore[22b]) | -6.03 | -5.69 | -5.53 | -3.74 | | |

*Fig. 13*

| Membrane Type | Log $K^{pol}_{c_{SJ}}$ | | | | | | | | |
|---|---|---|---|---|---|---|---|---|---|
| | $Ca^{2+}$ | $Li^+$ | $Na^+$ | $K^+$ | $H^+$ | $NH_4^+$ | $Ag^+$ | $N(Pr)_4^+$ | $N(Bu)_4^+$ |
| I (Fluorous) | -4.35 | -4.01 | -3.75 | -2.59 | -2.27 | -1.35 | +1.43 | +9.08 | +11.41 |
| II (Choroparaffin, KFPB) | -0.69 | -1.07 | -0.99 | -0.65 | -0.28 | -0.07 | +1.15 | +5.88 | +6.91 |

CHEMICAL SENSOR

CROSS-REFERENCE TO RELATED APPLICATIONS

This application claims priority to U.S. Provisional Application Ser. No. 60/684,765 filed on May 26, 2005. U.S. Provisional Application Ser. No. 60,684,765 is incorporated by reference herein.

STATEMENT REGARDING FEDERALLY SPONSORED RESEARCH OR DEVELOPMENT

Work relating to this document was supported in part by grants from the National Science Foundation (CTS-0428046) and the National Institutes of Health (1RO1EB005225-01). The United States government may have certain rights in the subject matter of the invention.

BACKGROUND

1. Field

The subject matter of the present invention relates to sensors. More particularly, the subject matter relates to sensors for detecting analytes.

2. Background

Conventional chemical sensors based on receptor-doped polymeric membranes (e.g., ion-selective electrodes or optical sensors) are routinely used worldwide in clinical medicine and chemistry. Every year, for example, over 200 million measurements of potassium in human blood samples are performed ex vivo with receptor-based ion-selective electrodes in hospital laboratories in the United States alone. Since also sodium, calcium, chloride, magnesium and carbonate are measured routinely in many blood samples, it is estimated that the clinical market represents over one billion measurements per year in the United States.

Conventional receptor-based chemical sensor membranes typically consist of receptors, lipophilic ions, and an inert polymer matrix. The polymer matrix is often plasticized (softened) with a compound of low molecular weight and high boiling point. The polymer matrix and plasticizer typically make up approximately 90% to 99% of the total membrane composition. Representative polymers are silicones, poly(vinyl chloride), and polyurethanes. For a review of conventional chemical sensors, see Bakker et al., *Chem. Rev.* 1997, 97, 3083; Bühlmann et al., *Chem. Rev.* 1998, 98, 1593; and Bakker et al., *Talanta*, 2004, 62, 843.

Unfortunately, these conventional sensors are prone to biofouling as a result of the various lipid, protein and other components present in biological samples such as blood and urine. These lipids, proteins and other components adsorbed onto, or extracted into, the sensor membranes (see Bühlmann et al., *Anal. Chem.* 2001, 73, 3199), causing "drifting" of the measured signal and requiring frequent replacement of the sensing membranes. Attempts have been made to reduce biofouling by counteracting surface adsorption, for example, by using membranes having modifications that cause them to release nitric oxide (Frost et al., *J. Am. Chem. Soc.* 2004 126(5), 1349; U.S. Pat. No. 6,841,166 (Zhang et al.; issued Jan. 11, 2005)). However, biofouling as a result of extraction or partitioning of lipids, fats, cholesterol, porphryrins and other hydrophobic and oily substances into conventional membranes remains a problem. A sensor with higher selectivity and/or reduced biofouling would represent a significant advance over existing technology for ex vivo monitoring. There is, in addition, a great need for implantable sensors (in vivo measurements) since none of the existing technologies has been shown to resist biofouling in vivo for much more than a few days.

BRIEF DESCRIPTION OF THE DRAWINGS

FIG. 12 shows Table 1 which provides ion pair formation constants in perfluoroperhydrophenanthrene containing tetrakis[3,5-bis(perfluorohexyl)-phenyl]borate and various cations.

FIG. 13 shows Table 2 which provides potentiometrically determined logarithmic selectivity coefficients, log $K^{pot}_{Cs,J}$, referenced to $Cs^+$ for fluorous ion exchanger, nonfluorous ion exchanger, and ionophore-based ion-selective electrode (ISE) membranes.

20(a), with the sensor communicating with the heart assist unit by transmitting a signal through an electromagnetic wave.

Figure 21:
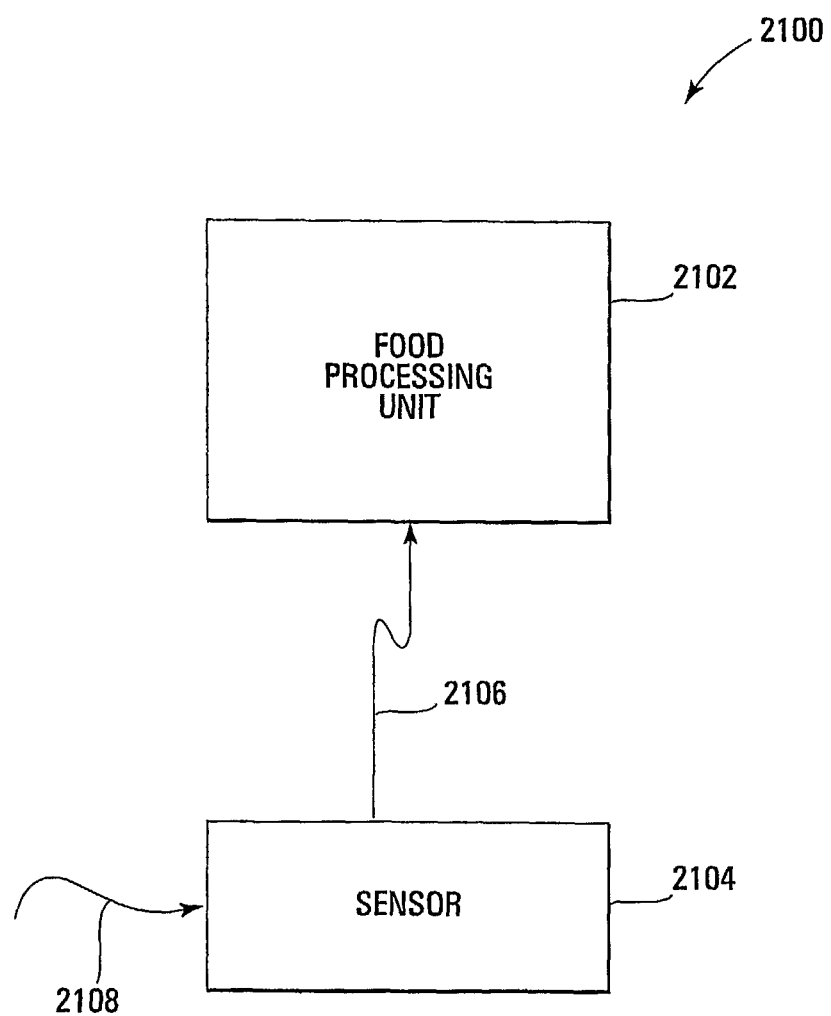

FIG. 21 shows a block diagram of an apparatus including a food processing unit and a sensor to generate a signal to control the food processing unit in accordance with some embodiments.

Figure 22:
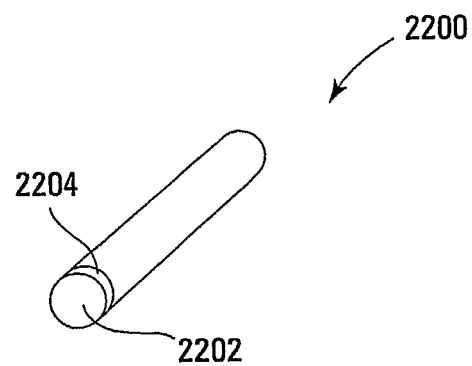

FIG. 22 is an illustration of an apparatus including an optically transmissive medium including a fluorous sensing phase in accordance with some embodiments.

Figure 23:
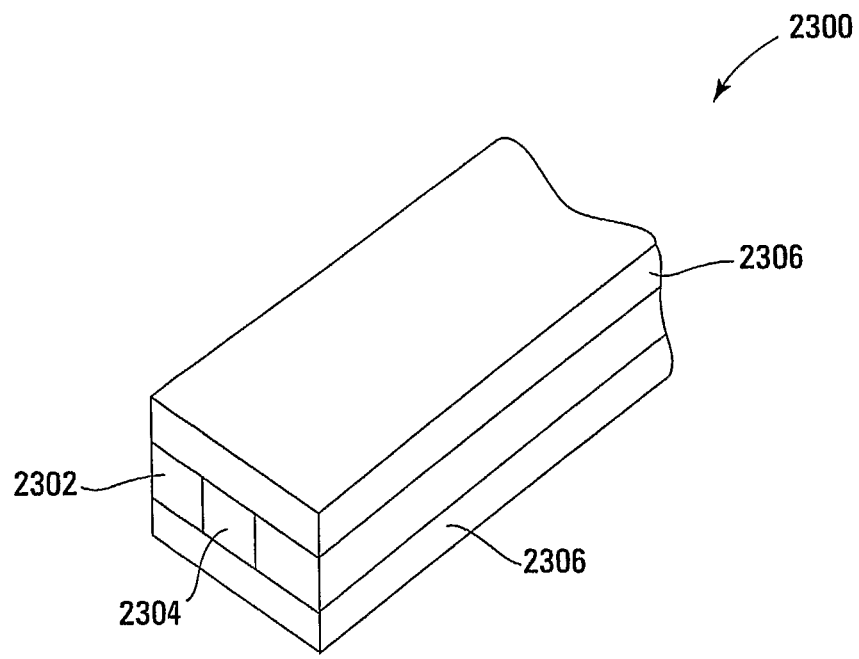

FIG. 23 is an illustration of an apparatus including a substrate including an optically transmissive medium having a fluorous phase sensor in accordance with some embodiments.

DESCRIPTION

The present invention provides chemical sensors that utilize a fluorous sensing phase. The sensors can be used to measure the concentration of one or more analytes in any fluid of interest. Fluids amenable to analysis using the chemical sensors of the invention can be either liquid, such as water, or gas, such as air. Examples of fluids that can be analyzed are biological fluids such as blood, blood products including blood fractions, serum, plasma, platelets and the like, urine, saliva, lymphatic fluid, cerebrospinal fluid, stomach fluid, exhalations and the like; environmental fluids or environmental samples such as air, water and soil extractions; and food samples such as dairy products and beverages. The analyte can be any charged or electrically neutral species that selectively binds to the fluorous sensing phase. Typically, the components of the fluorous sensing phase are selected so as to achieve selective binding of the analyte of interest.

The present invention encompasses not only the chemical sensors but also methods for making them and methods for using them to detect an analyte. This method is, of course, of considerable interest and value in the field of clinical chemistry and medicine. However, uses of the chemical sensor in many other fields are envisioned, as exemplified below.

"Fluorous" materials have a high fluorine content. The high fluorine content imparts the material with an extraordinarily low polarity, lower even than that of hydrocarbons. This unique property of fluorous phases makes them poor solvents for both hydrophilic compounds and for hydrophobic compounds that are typically soluble in hydrophobic phases such as oils. For example, the interferent stearic acid is four orders of magnitude less soluble in a fluorous solvent than a comparable non-fluorinated solvent of low polarity.

As a result of their fluorous nature, fluorous chemical sensing phases have very high chemical selectivities, and fluorous membranes are typically much less prone to biofouling than conventional sensing membranes. Materials such as lipids that are unintentionally extracted into conventional non-fluorous membranes of low polarity, thereby progressively fouling the membrane, will generally not be extracted into the fluorous sensing phase of a chemical sensor of the present invention. This significantly enhances the selectivity, robustness and lifetime of the chemical sensors used for ex vivo measurements in clinical medicine and chemistry. In addition, these characteristics are expected to facilitate development of implantable sensors for long term monitoring in the human or animal body. The use of chemical sensors based on fluorous phases will also permit novel uses of chemical sensors operated under harsh conditions, such as long term environmental monitoring with sensor networks (e.g., for the prediction of earthquakes), process control in the food industry, monitoring of the structural integrity of structures such as bridges, or in situ chemical sensing in boreholes in the oil industry.

It should be noted that the terms "fluorinated" and "fluorous" are not interchangeable. A molecule or polymer is fluorinated if it contains at least one fluorine atom. A highly fluorinated compound is considered fluorous, on the other hand, if it mixes neither with water nor an alkane but instead forms an immiscible three-phase system when mixed with an alkane and water. Typically, this happens when at least 60% of the molecular weight of a compound comes from fluorine. In some embodiments, a compound is considered fluorous when at least 70% of the molecular weight of the compound comes from fluorine. Compounds that contain somewhat less fluorine, for example compounds having between 50 wt % and 60 wt % fluorine, may also exhibit this behavior.

The chemical sensor of the invention includes a fluorous sensing phase that typically includes a highly fluorinated polymer (typically a perfluoropolymer, i.e., one in which all the hydrogen atoms that are bound to the carbon parent are replaced by fluorine atoms); an optional fluorous plasticizer; an optional fluorous receptor molecule; and an optional salt of a fluorous ion.

In a preferred embodiment, the chemical sensor contains a membrane or matrix formed from a highly fluorinated polymer; however, in an alternative embodiment, the fluorous sensing phase (which includes, for example, a fluorous receptor and/or the salt of a fluorous ion dissolved in a fluorous compound of low molecular weight) is trapped in an inert support material or a highly porous inert support material. Preferably, this support material is a porous perfluoropolymer, such as poly(tetrafluoroethylene), which is also known by the tradename Teflon®. In yet another alternative embodiment, the fluorous sensing phase is trapped in a highly porous inert support material even though the fluorous sensing phase (which includes, for example, a fluorous receptor and/or the salt of a fluorous ion dissolved in a mixture of a highly perfluorinated polymer and a fluorous compound of low molecular weight) already contains a highly perfluorinated polymer that provides it with some structural stability.

Optionally, the membranes used in the chemical sensor of the invention, whether made from a highly fluorinated polymer or a highly porous support material housing a fluorous sensing phase, can be surface modified to prevent adsorption of unwanted components of the sample containing the analyte to be detected. For example, the membrane can be derivatized in the same manner as conventional membranes, such as to release nitric oxide. (Frost et al., *J. Am. Chem. Soc.* 2004 126(5), 1349; U.S. Pat. No. 6,841,166 (Zhang et al., issued Jan. 11, 2005).

Fluoropolymer

The fluoropolymer is preferably insoluble in water and insoluble in oils, but it may be soluble in perfluorocarbon solvents such as perfluorohexanes or perfluoro(tributylamine). The fluoropolymer may be thermoplastic or elastic. In a preferred embodiment, the fluoropolymer has no or only a very low degree of crystallinity and permits fast diffusion of analyte (in free or complexed form) across the fluorous membrane (high diffusion coefficient). In a preferred embodiment, the polymer is amorphous and has a glass transition temperature below room temperature. Non-limiting examples of a non-elastic polymer are poly(perfluorobutenyl vinyl ether) or a copolymer of tetrafluoroethylene and 2,2-bis(trifluoromethyl)-4,5-difluoro-1,3-dioxole. A typical perfluoroelastomer contains linear poly(tetrafluoroethylene) chains copolymerized with perfluorinated monomers that carry side groups, such as a trifluoromethyl or perfluoroalkyl groups. Polymers of this class differ from one another mainly in the type and concentration of the side groups and the crosslinker. An example of such a polymer are the polymers obtained from copolymerization of perfluoro(methyl vinyl ether), tetrafluoroethylene and a low concentration of a substituted perfluorinated alkyl vinyl ether for crosslinking. Alternative embodiments may use elastic fluorosilicones or fluorinated polyphosphazines.

The highly fluorinated polymer may optionally include a functional group with one or several heteroatoms such as oxygen, nitrogen, or silicon. In a preferred embodiment, the heteroatoms (if any) do not interact chemically with any other membrane component or component of the sample. However, in an alternative embodiment, the polymer contains functional groups (which generally include heteroatoms) that act as receptor sites. For example, the receptor molecules may be covalently attached to the polymer.

Additionally, the highly fluorinated polymers used in this invention may give the membranes physical robustness against shearing, poking and other mechanical stress.

Plasticizer

Plasticizers are organic compounds of low molecular weight but high boiling points. Typically, the molecular weights of plasticizers are in the range of 500 to 20000. They are admixed to polymers to make them softer and prevent cracking or breaking. A primary requirement for a plasticizer is mutual miscibility with the polymer. Plasticizers enhance the flexibility of a plastic by increasing the freedom of movement of the polymeric macromolecules. Since plasticizers do not need to undergo any specific interaction with the polymer or any other compound, they may belong to various different compound classes. Due to the requirement of mutual miscibility with the fluoropolymer, a typical plasticizer used in this invention has a very high degree of fluorination. One typical class of plasticizers for this invention are linear perfluorocarbons such as perfluorooctane or perfluorononane, branched perfluorocarbons such as perfluoro(2-methyloctane), perfluorodecaline, cyclic perfluorocarbons such as perfluoroperhydrophenanthrene and perfluorodecalin, and mono perfluorocarbons. A plasticizer optionally includes a functional group with one or several heteroatoms such as oxygen, nitrogen, or silicon. Typical plasticizer with oxygens are, for example, linear or branched perfluoropolyethers such as $CF_3CF_2CF_2(OCF_2CF_2CF_2)_mOCF_2CF_3$ or $CF_3CF_2CF_2(OCF(CF_3)CF_2)_mOCHFCF_3$. Typical plasticizers with nitrogens are, for example, perfluoro(trialkylamines) such as perfluorotripentylamine or perfluorotrihexylamine, but also polyamines such as $CF_3CF_2(N(CF_3)CF_2CF_2)_mCF_2CF_3$. Typical plasticizers with silicon atoms are perfluoro(tetraalkylsilanes) such as perfluorotetrapentylsilane or perfluorotetrahexylsilane, but also compounds with multiple silicon atoms such as $CF_3CF_2(Si(CF_3)_2CF_2CF_2)_mCF_2CF_3$. In a preferred embodiment, the heteroatoms do not interact chemically with any other membrane component or component of the sample. However, in another embodiment, the plasticizer could also function as the receptor, typically through one or several optional functional groups containing heteroatom(s).

Receptor

The chemical selectivity of the chemical sensors of the invention preferably arises from a receptor molecule or group that selectively binds non-covalently or covalently to the analyte of interest. For a representative but incomplete review of many receptors used in chemical sensors, see Bühlmann et al., *Chem. Rev.* 1998, 98, 1593. These types of chemical sensors contain what is sometimes known as receptor-doped fluorous membranes. However, in an alternative embodiment, the chemical selectivity can be the result of molecular imprinting or inherent ion-exchange selectivity, as discussed in more detail below.

A receptor molecule that is included in a chemical sensor of the invention is typically highly fluorinated so that it is soluble in the highly fluorinated polymer. For example, a receptor molecule can be covalently modified to include one or more highly fluorinated linear, branched, or cyclic alkyl chains or other highly fluorinated species. These highly fluorinated species associate with the highly fluorinated polymers that form the fluorous membrane or, in the case of sensors that utilize porous, inert support material, with the highly fluorinated matrices present in the pores of the support material. Typically, highly fluorinated receptor molecules are made with steric and electronic considerations in mind so that the high degree of fluorination does not prevent, directly or indirectly, interaction of the receptor with the analyte. There may, for example, be an alkylene or arylene spacer between the receptor and a highly fluorinated alkyl chain. Typically, the noncovalent association between the highly fluorinated receptor molecule and the highly fluorinated polymer prevents the receptor molecule from leaving the sensing membrane.

Alternatively, instead of being modified to have a highly fluorous character itself, the receptor molecule can be covalently attached to the highly fluorinated polymers present in the fluorous phase of the chemical sensor. This is possible, for example, when the polymers contain reactive functional groups such as terminal hydroxyl groups, amino groups, carboxyl groups, and the like.

The covalent attachment of a receptor molecule to a highly fluorinated polymer having a reactive functional group preferably takes place in a perfluorinated solvent. However, at high temperature, fluorinated polymers can become soluble in certain nonfluorinated organic solvents, thereby facilitating the chemical attachment of receptor molecules. The synthesis of receptors is performed using the many methods known to those skilled in the art of organic chemistry.

It should be noted that some embodiments of the chemical sensor of the invention do not contain a receptor molecule. These embodiments are referred to herein as "receptor free." A fluorous phase that contains a membrane and a salt of a fluorophilic ion may possess "inherent" ion-exchanger selectivity. In addition to inherent receptor-free selectivity, fluorous membrane sensors of the invention may possess sensitivity as a result of molecular imprinting. Polymer precursors (e.g., monomers) can be combined with the analyte to be measured, then polymerized. After polymerization, the analyte is washed out of the polymer matrix, leaving a negative image in the form of a space that selectively binds the analyte.

Salt of a Fluorophilic Ion

The chemical sensor of the invention preferably includes in the fluorous phase the salt of a fluorophilic ion that is soluble therein. The fluorophilic ion is typically a fairly large organic species and can be an anion (negatively charged) or a cation (positively charged). At the point of sensor membrane preparation, the counterion is a small hydrophilic ion, such as $Li^+$, $Na^+$, $Mg^{2+}$, $Cl^-$, or $SO_4^{2-}$, or any analyte ion for which the sensor membrane is designed to be selective for. One role for this salt in the chemical sensor of the invention is to provide a counter ion for the analyte if the ionophore (ion receptor) in the chemical sensor is a neutral molecule. For example, the ionophore for $K^+$ may be a neutral molecule. When it complexes with $K^+$, the resulting complex is positively charged. A suitable salt of a highly fluorinated anion would have a hydrophilic cation that is readily replaced in the fluorous membrane by $K^+$, while the highly fluorinated cation would remain in the fluorous sensing membrane and serve as a counterion to the complex.

The use of a fluorophilic anion or cation in an ion selective sensor of the invention has additional advantages. It can, for example, help the researcher control the stoichiometries of the receptor complexes. By changing the ratio of fluorophilic ion to receptor molecule, the number of receptor molecules that bind an analyte molecule can be changed. For example, if 1:2 complexes of an electrically neutral receptor with a singly charged analyte cation (analyte:receptor) are desired, the chemical sensor can be loaded with a 1:2 ratio (fluorophilic ion:receptor) of fluorophilic anion. This strategy can be employed for both charged and neutral ionophores (ion receptors; see, for example, Amemiya, S. et al., *Anal. Chem.* 2000, 72, 1618). In the case of an electrically charged ionophore, the counter ion of the fluorophilic ion may be the charged ionophore (see Amemiya, S. et al., *Anal. Chem.* 2000, 72, 1618). Use of a fluorophilic ion (in the form of a salt of a fluorous ion) is optional, and some selectivity for the analyte typically occurs in its absence; however, it is preferable to include (i.e., dope) a salt of a fluorous ion in the chemical sensor membrane as it typically allows for increased sensitivity by stoichiometric optimization.

Analyte Detection

The analyte bound by the chemical sensor is preferably detected either electrically or optically. Electrical detection can, for example, take the form of potentiometric detection (based on a change in electrical potential) or amperometric detection (based on a change in the flow of electrical current through the sensor). When potentiometric detection is used, the analyte is a charged species, i.e., an ion, and the sensors are typically referred to as ion-selective electrodes. When amperometric detection is used, the analyte must also be a charged species. If receptor molecules that bind ions are used, these receptor molecules are often referred to as ionophores. The receptor is selective for the ion of interest, for example sodium, calcium, chloride, magnesium or carbonate, which are commonly measured in clinical chemistry.

Because the fluorous phase of the chemical sensor has such a low polarity, the resistance across the membranes or matrix may be higher than that observed for conventional membranes. Resistance can be lowered, if desired, by introducing into the membrane a salt consisting of a highly hydrophobic cation and anion. This increases the electrical conductivity of the sensing membrane and reduces electric noise. It may also be used to fine-tune the selectivity. Typically, one or both of the cationic and anionic components of the salt are highly fluorinated compounds.

Optical detection can be used to detect charged or neutral analytes. When optical detection is used, the chemical sensors are typically referred to as optodes or optrodes. In one method of optical detection, the receptor molecule changes color, or produces some other spectroscopically or spectrophotometrically detectable change, upon binding a charged or electrically neutral analyte. If the analyte is ionic and the receptor changes color upon analyte binding, the receptor is called a chromoionophore. Alternatively, a highly fluorinated dye can be added into the membrane to detect the co-extraction into the membrane of an ion of opposite charge sign of the analyte ion, or the ion-exchange of an ion with the same charge sign as the analyte ion. For example, an optical $Cl^-$ sensor doped with a $Cl^-$ selective receptor could respond with a color change to the uptake of $Cl^-$ and $H^+$ into the sensing phase because the $H^+$ binds selectively to a chromoionophore selective for $H^+$. Indeed, the fluorous sensing phases of the chemical sensor of this invention are particularly well suited to optical detection, since many perfluoropolymers and other fluorous compounds are transparent to ultraviolet light down to 180 nm and less.

Membrane Electrode Measuring Circuit

Figure 1:
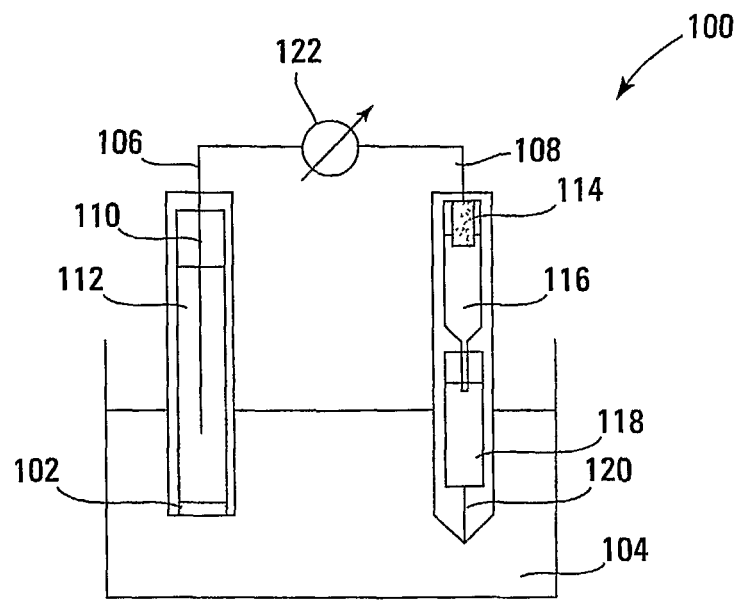
FIG. 1 is a schematic diagram of a membrane electrode measuring circuit and cell assembly, including an ion-selective membrane, immersed in a sample.

FIG. 1 is a schematic diagram of a potentiometric membrane electrode measuring circuit and cell assembly 100, including an ion-selective membrane 102, immersed in a sample 104. The membrane electrode measuring circuit and cell assembly 100 includes an ion-selective electrode 106 and a reference electrode 108. The ion-selective electrode 106 includes Ag/AgCl electrode 110 in contact with an inner filling solution 112, the ion-selective membrane 102 in contact with the inner filling solution 112, and the sample 104. (As it is known to those skilled in the art of electrochemistry, the Ag/AgCl electrode can be readily replaced by another inner reference electrode.) The reference electrode includes an electrode 114 immersed in a reference electrolyte 116 coupled to a bridge electrolyte 118 coupled to the sample 104 through a liquid junction, such as a capillary 120. The membrane electrode measuring circuit and cell assembly 100 is not limited to a particular mechanical configuration or fabrication using particular materials. The mechanical configuration and materials can be modified to meet the constraints of a particular application. In operation, the membrane electrode measuring circuit and cell assembly 100 develops an electromotive force between the ion-selective electrode 106 and the reference electrode 108. The electromotive force can be displayed on a voltmeter 122. The measured voltage can indicate the presence or absence of a target material in the sample.

Figure 2:
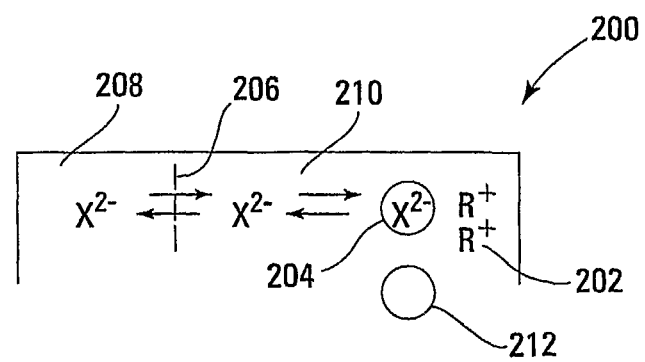
FIG. 2 is a schematic diagram of a receptor-doped membrane suitable for use in connection with the membrane electrode measuring circuit and cell assembly shown in FIG. 1.

FIG. 2 is a schematic diagram of a typical receptor-doped membrane 200 suitable for use in connection with the membrane electrode measuring circuit and cell assembly 100 shown in FIG. 1. The very hydrophobic ions $R^+$ (cationic sites) 202 are the co-ions of the electrically charged complexes 204 and, thereby, control receptor complex stoichiometry. The junction or boundary 206 allows the transfer of ions between the aqueous phase 208 and the organic phase 210. The organic phase also includes free receptors 212.

The membrane electrode and measuring circuit, shown in FIG. 1 is suitable for use in connection with the membranes described below.

EXAMPLES

The present invention is illustrated by the following examples. It is to be understood that the particular examples, materials, amounts, and procedures are to be interpreted broadly in accordance with the scope and spirit of the invention as set forth herein.

As described in more detail below, we have investigated the selectivity of receptor-free cation exchanger electrodes based on fluorous membranes. A dramatic increase in the range of selectivities relative to conventional in-exchange electrodes of more than seven orders of magnitude was found. A receptor-based ion-selective electrode was fabricated based on a fluorous membrane, as further described below.

Example 1

Sensors

Perfluorinated Matrixes as New Materials for Receptor-Doped Chemical Sensors with Robustness and Selectivity Perfluorocarbons have properties that distinguish them from other organic compounds. For example, generations of chemists were taught that "like dissolves like" signifies that polar solvents such as water are miscible with other polar solvents, and nonpolar solvents such as hexane are miscible with nonpolar solvents. It is less known that many perfluorocarbons are not miscible with hydrocarbons precisely because hydrocarbons are too polar. In contrast to the common conception of alkanes as the typical nonpolar solvents, alkanes are more polarizable than perfluorocarbons. On the $\pi^*$ scale of solvent polarity, water has a $\pi^*$ value of 1, hexane defines 0, and perfluorooctane has the value of −0.41. The combination of chemical inertness and (ultimate) non-polarity makes perfluorinated phases useful in the development of chemical sensors based on receptor-doped polymeric membranes.

Potentiometric Sensors Based on Fluorous Membranes

The key components of receptor-based sensors are the lipophilic receptors that are capable of selectively and reversibly binding analyte ions. They are usually called ionophores or ion carriers. For routine measurements, these receptors are incorporated into a polymeric membrane, which is placed between the sample and an electrode-internal solution contacted to an internal reference electrode (FIG. 1). The membrane can be considered as a water-immiscible phase in which the receptor and receptor complexes move by diffusion, which allows for equilibration of the ion transfer at the phase boundary to the sample (FIG. 2) and the establishment of the potentiometric response as the result of analyte-dependent phase boundary potential. Besides the receptor, the membrane contains commonly a lipophilic ion that is used to control the stoichiometry of the analyte-receptor complex. The thus prepared electrode responds to the activity of the target ion in the sample. Its selectivity is related to the equilibrium constant of the exchange reaction of target and interfering ions between the organic and aqueous phases. It strongly depends on the ratio of complex formation constants of these ions with the ionophore in the membrane phase.

An ion selective electrode (ISE) membrane suitable for use in connection with the present invention should exhibit several properties. First, the ISE membrane should be immiscible with water. Second, it should dissolve the receptor and permit fast ion exchange at the sample-membrane phase boundary. Third, it should have a sufficiently low electrical resistance to permit potentiometric measurements. Fourth, it should offer only a very low solubility to lipophilic sample components.

These requirements can be met by fluorous phases. The term "fluorous" refers to highly fluorinated solvents and polymers and emphasizes—in analogy to "aqueous"—the peculiar character of fluorinated phases. It is exemplified by the unique properties of perfluorocarbons, which do not fit into the simplistic view of polar vs. nonpolar solvents ("like dissolves like"). On one hand, perfluorocarbons are immiscible with polar solvents such as water, as expected for solvents with a low dielectric constant. Indeed, the solubility of perfluorocarbons in water is extremely limited ($10^{-6}$ to $10^{-10}$ mL/mL for a series of compounds with 5 to 10 carbon atoms). On the other hand, many perfluorocarbons are also immiscible with many typical nonpolar solvents such as higher alkanes, despite their similarly low dielectric constants. At room temperature, perfluoroalkanes with seven or more carbon atoms are not miscible with the corresponding alkanes, and the free energy of transfer of a $CH_2$ group from a hydrocarbon into a fluorocarbon phase is about one third of the energy required for the transfer of a $CH_2$ group from a hydrocarbon into water. Indeed, fluorocarbons have the lowest polarities of all known solvents.

This unique difference is explained by the extremely low polarizability of the carbon-fluorine bond, which results from the high electronegativity of fluorine that does not permit polarization. Induced dipoles in perfluorocarbons are very small. While alkane molecules interact with one another through significant induced dipole/induced dipole interactions (London forces), this type of interaction is much weaker between perfluorocarbons. Indeed, on the $\pi^*$ scale of solvent polarity, water has a $\pi^*$ value of 1.09, cyclohexane defines 0, and perfluorooctane has the astounding value of −0.41. This effect is also evident from the boiling points of alkanes and perfluoroalkanes. While hexane and perfluorohexane have similar boiling points (68 and 56° C., respectively), the molecular weight of the latter is 3.9 times larger. Another manifestation of the weak interaction between fluorocarbons is their comparatively high compressibility, which reflects the ease with which intermolecular voids can be formed in fluorocarbons. This is also one of the reasons for the high solubility of oxygen in fluorocarbons, and the basis for their use as blood substitutes (see below). Another reason for the high solubility of oxygen is related to the size of the fluorine atom. With a van der Waals radius of 147 pm, fluorine is about 27 pm larger than the hydrogen atom. As a result of this size, perfluoroalkyl chains are less flexible than alkyl chains, and adopt a helical conformation differing significantly from the typical gauche/trans conformation alkanes.

Because of an interest to use perfluorocarbons not only for oxygen transport but also for drug delivery, the solubility of a number of biologically relevant compounds has been measured in fluorocarbons. These data confirm that sugars, amino acids, and a number of carboxylic acids have very low solubility in perfluorocarbons. As an interesting manifestation of the unique character of perfluorocarbons, the solubility of alkanoic acids actually decreases with the length of the alkyl chain. Clearly, this is the result of the lipophobicity of the fluorous phase.

The properties of perfluorocarbon materials observed in medical application are compatible with their use as fluorous matrixes for chemical sensors. Perfluorocarbons have no known toxicity. While adsorption of hydrophobic substances to hydrophobic perfluorinated surfaces is not surprising, cell attachment is inhibited to a surprising extent, and might be further enhanced if necessary by the incorporation of NO releasing agents.

Interferences from Electrically Neutral, Lipophilic Compounds

Hydrophobic compounds interfere with the operation of receptor based sensors. An ISE responds to a target ion (=analyte) and to interfering ions with the same charge sign as the target ion. Interferences from ions of the opposite charge sign are usually limited to samples with high activities of lipophilic co-ions. Electrically neutral species are ordinarily not considered as interferents. However, nonionic species can affect emf responses significantly. For example, the effect of nonionic analytes on the activity of an ion in the sample was used to determine water in methanol, acetic acid, or acetonitrile, and ethanol in alcoholic beverages. A second type of effects of nonionic compounds on emf responses occurs only in the case of liquid and polymeric membrane electrodes. These effects arise when a nonionic compound partitions into a hydrophobic sensing membrane and, directly or indirectly, affects the membrane activity of the potential-determining (analyte) ions, which are distributed across the sample-membrane interface. For example, poly(vinyl chloride) membranes containing tetraphenylborate salts of barium complexes with polyethoxylates originally developed as $Ba^{2+}$-selective electrodes, respond to various acyclic polyethertype nonionic surfactants. Valinomycin- and crown ether-based electrodes respond to higher alcohols and dinitrophenol, and several anion-selective electrodes were found to respond to phenols. Blood gas/electrolyte analyzers commonly operate with calibration and wash solutions that contain nonionic surfactants (e.g., polyether-based compounds). It has been shown that concentrations of nonionic surfactants as low as $5.5 \cdot 10^{-5}$ M affected emf responses of cation selective electrodes. The response to these surfactants was modeled, changes in selectivities were discussed, and it was reported that optical results confirm that nonionic surfactants affect the emf response by partitioning into the sensor membrane and directly interacting with the analytes and the ionophore.

Figure 3:
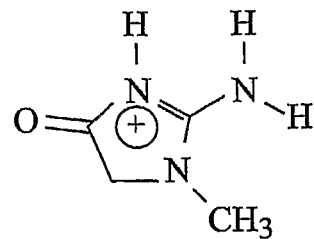
FIG. 3 illustrates the structure of protonated creatinine.

An unexpected interference was observed in measurements of creatinine. The creatinine concentration in urine is routinely used to assess kidney health, which is of major interest to the physician not only because of kidney diseases but for the determination of dosages of toxic drugs as they are used, for example, in the treatment of cancer or HIV. FIG. 3 illustrates the structure of the protonated creatinine (creatininium). Ionophore-based ISEs for creatininium were reported, but have so far not been satisfactory enough for measurements in clinical chemistry. Bühlmann et al. (*Anal. Chem.* 2001, 73, 3199) have shown that relatively simply creatininium ISEs based on ion exchanger membranes exhibit remarkably high selectivities for creatininium. However, measurements in diluted urine samples showed unacceptable large emf drifts. Potentiometric, chromatographic, NMR, and mass spectrometric evidence did not reveal any major cationic interferents, and anionic interferents cannot trivially explain the consistently positive nature of the emf drifts. Ultrafiltration of urine samples showed that the interferents have molecular weights below 1000 amu. The drifts are apparently caused by electrically neutral lipophilic compounds of low molecular weight, which are easily extracted into organic phases. Follow-up experiments showed that p-cresol and cholesterol in physiological concentrations cause no significant emf responses. However, coproporphyrin, phosphatidylserine, taurocholic acid, cholic acid, phosphatidylethanolamine, and octanoic acid, cause positive emf drifts of the type that were observed with the urine samples. The extent of the responses and the response time depended not only on the type of compounds but also on the measured cation. These results suggest that the emf drifts are due to extraction of natural lipids into the hydrophobic membrane phase, where they interact in an ionophore-like fashion with the analyte and interfering ions. Changes in the potentiometric selectivities after contact with natural lipids support his interpretation. The same effect of natural lipids is also expected for ionophore-based electrodes. Indeed, exposure of a valinomycin-based electrode to an extract of urine resulted in a significant reduction of the Na$^+$ discrimination, increasing the logarithm of the selectivity coefficient, $\log K^{pot}_{K,Na}$, from −3.9 to −3.1.

Food Samples

While there is a considerable interest from the food industry to determine various analytes using ion-selective electrodes (ISEs), only few reports describe their use for direct measurements in food. Bühlmann et al. investigated the suitability of glass electrodes and ionophore-based solvent polymeric ISEs for the determination of pH in Process cheese, Cheddar cheese and milk (*Talanta*, 2004, 63, 139). While the protein rennet casein posed no problems in pH measurements, the extraction of electrically neutral lipophilic compounds or hydrophobic peptides into receptor-doped polymeric membranes did pose problems. ISEs based on tridodecylamine (R,N) as ionophore, o-nitrophenyl octyl ether (oNPOE) as plasticizer, and poly(vinyl chloride) (PVC) as plasticizer could only be used to measure the pH of diluted Process cheese after desensitization of the electrodes in a cheese emulsion. To determine if the selectivity for R,N membranes deteriorates upon prolonged exposure to cheese, selectivities for monovalent cations (Na$^+$, K$^+$, and Li$^+$) were measured before and after 48 h of exposure of R,N membranes to 20% and 100% Process cheese emulsions. Indeed, the selectivity coefficients for Na$^+$ and K$^+$ worsened by up to two orders of magnitude upon exposure to cheese, and similarly unfavorable changes were observed for Li$^+$ too. To explore if lipids are the cause of this selectivity loss, membranes were exposed to a lipid extract for about 24 hours. A similar decrease in selectivity to cations as observed upon exposure of electrodes to 100% cheese was obtained. Moreover, there was a significant increase in the membrane resistance of up to an order of magnitude upon exposure to cheese. For example, the resistance of a R$_3$N/oNPOE membranes rose form 0.3 MΩ to 3.2 MΩ.

In view of the selectivity losses of PVC-based membranes upon exposure to cheese, Bühlmann et al. also explored the use of silicone rubber membranes, which were previously reported for measurements of body fluids with significant protein and lipid components. Silicone membranes were exposed for about 48 hours to 20% Process cheese emulsions. After exposure to Process cheese emulsions, the discrimination of potassium deteriorated from $\log K^{pot}_{H+,K+}$ −11.5 to −8.9. These results show that the plasticized silicone membranes behave similarly to PVC membranes. It has been reported that silicone rubber fails mechanically as a result of the sorption of lipids and their oxidation products.

Fluorous Phases

In tests of low-polarity fluorinated phases for chemical sensing, liquid perfluorocarbons were used as membrane matrixes. One of the first tested solvents was perfluoroperhydrophenathrene (PFPHP) since it has a high boiling point and is a liquid at room temperature. Non-branched perfluoroalkanes are typically solids at room temperature or have a low boiling point. Perfluorination was confirmed by a $^1$H NMR spectrum of neat PFPHP, which did not reveal any significant hydrogen bearing impurities.

Since perfluorocarbon solvents cannot support their own weight, highly porous poly(tetrafluoroethylene) (PTFE) filter membranes (thickness 0.125 mm, porosity 68%, pore size 10 μm) were soaked with the doped perfluorocarbons of interest. These membranes were then mounted into a custom-made body made of the chemically highly resistant poly(chlorotrifluoroethylene) (known as PCTFE, Kel-F®, or Neoflon®) which does not swell even in perfluorocarbon solvents, and is easier to machine than PTFE. The shape of this body remembers that of the often used Phillips electrode bodies (see FIG. 1), with an inner filling solution and an inner Ag/AgCl reference electrode.

Since these PTFE membranes have no backing to improve their mechanical stability, a contamination of the liquid fluorous phase with impurities was not expected. Ionic impurities in PVC are well known to affect potentiometric responses. Indeed, when PTFE membranes soaked with pure PFPHP were mounted into the bodies and immersed into 1 M KCl solutions, the electrical resistance of the electrodes was found to be too high to be measured (>>10 G ohms), confirming the absence ionic impurities in the PFPHP phase. In contrast, when a PTFE membrane not soaked with a fluorous phase was mounted into the body, the resistance measured without the PFTE membrane was very low. This shows that the perfluorocarbon phase supported by the porous PTFE membrane is continuous throughout the porous support.

Subsequently, PFPHP was saturated with a number of lipophilic salts that are often used as sources of ionic sites for receptor-based ISEs, and the resistance of porous PTFE membranes soaked with these solutions were tested. However, the resistances of all tested membranes were too high to be quantified. This showed that sodium tetrakis(3,5-bis(hexafluoro-2-methoxy-2-propyl)phenyl)borate, sodium tetrakis-(3,5-bis(trifluoromethyl)phenyl)borate, and tridodecylmethylammonium chloride are all not soluble enough in PFPHP to make potentiometric measurements with fluorous phases possible. Not even the lithium salt of perfluorinated tetrakis(pentafluorophenyl)borate was soluble enough, despite the presence of twenty fluorine atoms in the anion of this salt. Also, the highly lipophilic electrolyte salt ETH 500 (tetradecylammonim tetrakis[p-chlorophenyl]borate) was not sufficiently soluble in PFFHP. The series of experiments was repeated with perfluoro(tributylamine), but again none of the investigated salts was found to be soluble enough in the fluorous phase.

To explore the possibility that salts of ionic sites might be more soluble in fluorous phases if their hydrophilic ion were complexed to a receptor, the solubilities of several ion receptors in PFPHP and perfluoro(tributylamine) were tested. However, the $K^+$ ionophore valinomycin, the $Ag^+$ ionophore dibenzyl sulfide, the $H^+$ inonophores tridodecylamine, Hydrogen Ionophre IV, and Chromoionophroes I, II, and III (all Fluka AG, Buchs, Switzerland), the sulfate ionophore α,α'-bis(N'-phenylthioureylene)-m-xylene and the hydrogen-bonding and the partially fluorinated compound tetrakis(trifluoromethyl)-1,3-benzenedimethanol were all found to be poorly soluble in these PFPHP and perfluoro(tributylamine).

These result show that commercially available ionic sites, lipophilic electrolyte salts and receptors are not suitable for potentiometric measurements with fluorous phases. The very fact that all these lipophilic salts and ionophores are not appreciably soluble in PFPHP and perfluoro(tributylamine) confirm the promise of fluorous phases for chemical sensor membranes. Just as these compounds too, ionic and electrically neutral interferents that would interfere with sensors based on other membranes phases will not be extracted into fluorous phases and will not interfere with chemical sensors based on fluorous membranes unless they can interact specifically with the fluorophilic receptors; in such a case better receptors would have to be prepared.

Fluorophilic Cationic and Anionic Sites

A salt that is soluble in a fluorous phase has to have a cation or an anion with perfluoroalkyl substituents, or both. In the case of a salt designed to provide lipophilic ionic sites that act as counterions to the complex of a receptor (see FIG. 2), the fluorophilicity must reside on only one ion. The co-ion is of little importance since that comparatively hydrophilic co-ion must be readily replaced by analyte ions in the conditioning process preceding the first application of the sensor. This conditioning process involves insertion of the freshly prepared sensor membrane into a solution of the analyte ion, which causes the spontaneous the transfer of analyte ion into the sensing membrane and release of the originally present co-ions into the aqueous conditioning solution.

Figure 4:
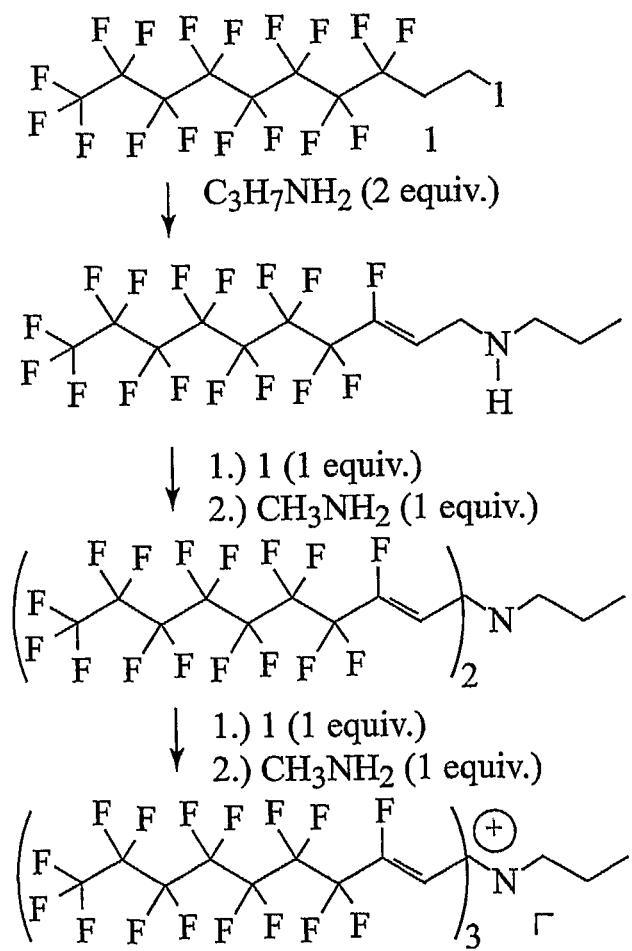
FIG. 4 illustrates steps for the preparation of a fluorophilic tetraalkylammonium ion with a sufficient fluorophilicity to make it suitable as cationic sites for potentiometric sensors.

FIG. 4 illustrates steps for the preparation of a fluorophilic tetraalkylammonium ion with a sufficient fluorophilicity to make it suitable as cationic sites for potentiometric sensors. The use of $(CH_2)_2$ spacer between the perfluorinated alkyl chain and the iodide has several reasons. If no spacer were used, the intermediate tertiary amine would have such a low reactivity towards alkylation that the last step would be impossible. The use of a $(CH_2)_1$ spacer is not desirable since compounds with the structure $R_fCH_2N^+(CH_3)_3$ were reported to be unstable. The use of a $(CH_2)_{n>2}$ spacer to the nitrogen is conceivable but introduces many nonfluorinated $CH_2$ groups. In experiments, it was found that the use of two equivalents of the amine leads to the spontaneous HF elimination at room temperature as a follow-up reaction in step one (see scheme in FIG. 4). This reaction will not be suppressed, since the same reaction might occur in a sensing membrane and cause the decomposition of the sensing membranes during their use. Instead, this IF elimination will be encouraged by addition of an additional equivalent of amine at the end of each alkylation step, giving the more stable $R_fCF=CHCH_2$ substituted amines and, in the final step, ammonium salt.

If necessary, this synthesis plan can be modified. In one embodiment, the iodide 1 is replaced with a more reactive tosylate, which can be obtained from tosyl chloride and the corresponding partially fluorinated alcohol. If only the quaternization step of the above synthesis is inefficient, the steric hindrance of the tertiary amine can be reduced by replacing in step 1 the propylamine with methylamine. Alternatively, the flexibility of the partially fluorinated alkyl chains may be improved by replacing the $R_f(CH_2)_2$ with a $R_f(CH_2)_3$ group.

In another alternative embodiment, one, two, three or four of the alkyl substituents of the tetraalkylammonium salt could be replaced with an unsubstituted or substituted phenyl group, and the nitrogen atom may be replaced with a phosphorus atom, resulting in a phosphonium cation. As a representative case, Example 3 below gives details for the methyltris[3,5-bis(perfluorooctylpropyl)phenyl]phosphonium cation.

Figure 5:
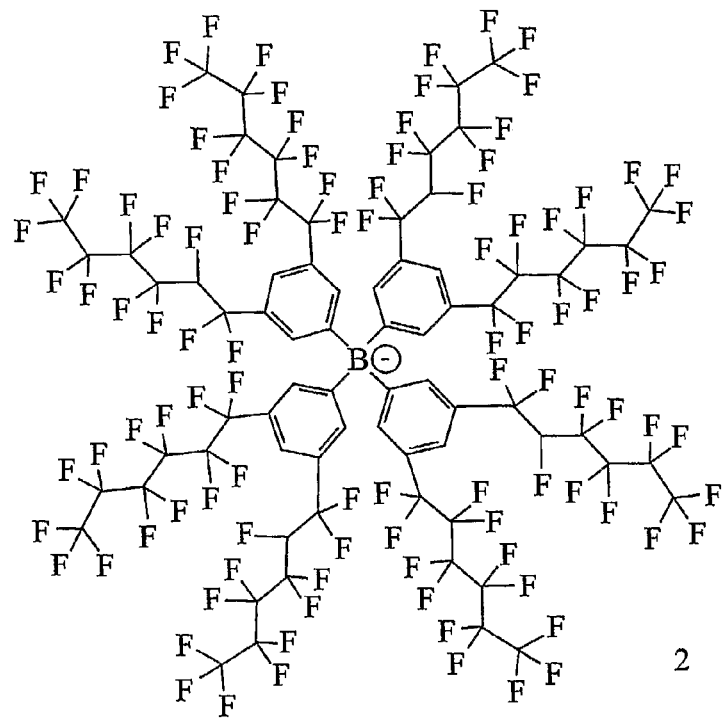
FIG. 5 illustrates the structure of tetrakis[3.5-bis(perfluorohexyl)phenyl]borate.

One example of a reported fluorophilic anion is tetraphenyl-borate substituted with a total of eight perfluorohexyl substituents, i.e., tetrakis[3,5-bis(perfluorohexyl)-phenyl]borate, 2, shown in FIG. 5. Two salts of 2 were reported to be soluble in fluorous phases. The salts of 2 with sodium and the salt of 2 with a cationic rhodium diphosphine complex were found to be soluble in perfluoro(butyltetrahydrofuran). In one embodiment, the sodium salt of 2 is prepared from 1,3-diiodobenzene by perfluoroalkylation with perfluorohexyliodide and $Cu^o$, introduction of a bromo substituent in the 5-position, and conversion to the tetraphenylborate derivative by reaction with butyl lithium and $BCl_3$. Bühlmann et al. have also prepared analogous salts where the perfluorohexyl groups were replaced by perfluorooctyl groups or perfluorodecyl groups. The preparation of analogous compounds with other straight chain perfluoroalkyl, branched perfluoroalkyl, and perfluorocycloalkyl groups according to similar synthesis procedures are obvious to those skilled in the art of organic synthesis.

Fluorophilic Electrolyte Salt

Ion pairing in nonpolar solvents is significant, but appropriate lipophilic electrolyte salts provide for a sufficient conductivity to make voltammetric experiments in such solvents possible. For example, the oxidation of ferrocene and the reduction of buckminsterfullerene ($C_{60}$) and p-dicyanobenzene were successfully examined in benzene (dielectric constant, $\in$, 2.27) using tetra-n-hexylammonium perchlorate as electrolyte, despite the fact that less than 1% of this electrolyte is dissociated in this solvent. Ion pairing in fluorous phases may be very strong and the electrical resistances so large that potentiometric measurements are difficult despite the fact that all membrane components are dissolved. A fluorophilic electrolyte salt consisting of a fluorophilic cation and a fluorophilic anion reduces the resistance of ionophore-doped fluorous sensing membranes. Moreover, the availability of such a fluorous electrolyte salt makes voltammetric studies and electrochemical syntheses in fluorous phases possible.

Such a salt can be prepared by metathesis from the fluorophilic tetraalkylammonium sodium salt described above and sodium tetrakis[3,5-bis(perfluorohexyl)phenyl]borate. For example, the fluorophilic electrolyte salt tris(perfluorooctylpropyl)methylammonium tetrakis[3,5-bis(perfluorohexyl)phenyl]borate was prepared. It was found to be an ionic liquid with a glass transition temperature, $T_g$, of −18.5° C. Interestingly, the molar conductivity of solutions of this salt increases very steeply in the high concentration range, making it a particularly effective electrolyte salt (Bühlmann et al. *J. Am. Chem. Soc.*, 2005, 127, 16976).

Figure 6:
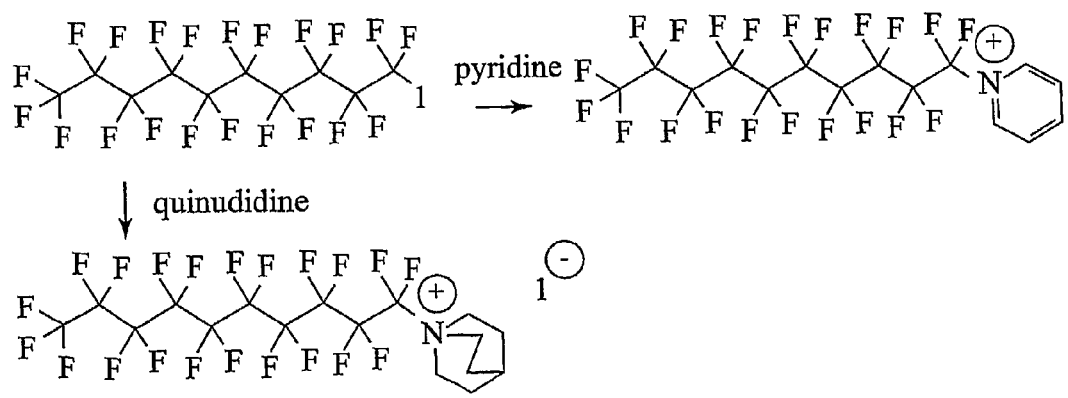
FIG. 6 illustrates reactions for obtaining fluorophilic cations.
Figure 7:
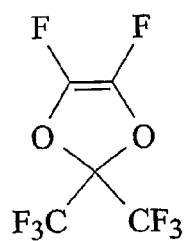
FIG. 7 illustrates the structure of 2,2-bis(trifluoromethyl)-4,5-difluoro-1,3-dioxole.

In an alternative embodiment, such a salt can be prepared by metathesis from a fluorophilic phosphonium salt (as described above and in Example 3) and a tetrakis[3,5-bis(perfluoroalkyl)phenyl]borate. The disadvantage of these two approaches is that the synthesis of such fluorophilic electrolyte salts is cumbersome because it typically requires a total of about six steps when accounting for the synthesis of both the cation and the anion. However, this effort is not always necessary since a fluorophilic electrolyte salt does not need to be composed of a cation and anion that each have a fluorophilicity as high as the ionic site salts described above. The cation and anion of a fluorophilic electrolyte salt both contribute to fluorophilicity and, therefore, the fluorophilicity of each of these ions does not need to be as high as in the case of the fluorophilic cationic and ionic sites described above. To find a readily available fluorophilic electrolyte salt, a number of salts can be prepared. As the source for fluorophilic anions, commercially available tetraphenylborate derivatives, such as tetrakis(pentafluorophenyl)borate and tetrakis[3,5-bis(trifluoromethyl)phenyl]borate salts, can be used. The source of the fluorophilic cations can be the fluorophilic ammonium or phosphonium cations as described above and in Example 3. Alternatively, suitable but less fluorophilic cations can be obtained using simpler syntheses by reaction of perfluoroalkyl iodides with tertiary amines or pyridines. The scheme shown in FIG. 6 shows two examples. The non-aromatic example has been synthesized. Using metatheses, a number of fluorophilic electrolyte salts can be prepared from such quaternary ammonium ions and commercial fluorophilic anion salts.

Cyclic voltammetry measured with a fluorous solvent, as described herein, is a major benchmark for nonaqueous electrochemistry. The use of organic solvents is not only of mechanistic interest, but widens the range of accessible potentials and makes it possible to measure the electrochemical properties of compounds that are insoluble or unstable in water. Moreover, the nonaqueous solvents have become crucial for the development of high energy density batteries. While the use of polar organic solvents has been the focus of numerous studies, the utilization of solvents as nonpolar as benzene, mesitylene or hexane is the exception. In particular, there has so far not been any demonstration of an electroanalytical experiment performed with a saturated perfluorocarbon solvent. The most nonpolar solvent used is (trifluoromethyl)benzene, which takes an intermediate position between hydrocarbons and perfluorinated solvents. Importantly, the demonstration of voltammograms with a fluorous solvent will not only extend the range of organic solvents that can be used in electrochemistry. Because perfluorocarbons have the lowest polarities of all known solvents, these cyclic voltammograms will demonstrate the limit of electrochemistry with nonaqueous solvents.

Selectivity of Receptor-Free Ion Exchange Membranes

To achieve potentiometry with fluorous phases, the selectivity of receptor-free cation and anion-exchanger electrodes based on the fluorophilic sites and non-polymeric phases was determined. The maximum gain in potentiometric selectivity that can be obtained by using fluorous phases was identified, and the selectivity-modifying effect of heteroatoms in the structure of perfluorocarbons was assessed.

Perfluorocarbons are suitable for use as matrixes for potentiometric sensors because of the negligible solvation of interfering ions in these phases. A potentiometric sensor is selective for the ion of interest (i.e., the analyte ion) if the transfer of this ion from the aqueous sample into the sensor membrane phase is more favorable than for an interfering ion (c.f. FIG. 2). Different methods can be used to achieve this result. In one embodiment, the phase transfer of the ion of interest is made more favorable by the design of a receptor that strongly (and selectively) binds the ion of interest in the membranes phase. In some embodiments, this effort is enhanced by the control of the stoichiometry of the complexes of the receptor with the primary ion. In another embodiment, favorable interactions between the interfering ion and components of the sensing membrane are reduced. This reduction includes the minimization of ion-pair interactions with the ionic sites, and the minimization of the solvation of interfering ions by the polymer matrix and plasticizers. One example of the latter is the selectivity of $H^+$-selective electrodes. Thus, when o-nitrophenyl octyl ether was used as a membrane plasticizer (≈⅔ of the total membrane weight) instead of the equally popular plasticizer bis(2-ethylhexyl) sebacate and using the same ionophore and polymer matrix, approximately three orders of magnitude higher selectivity for $H^+$ over was achieved. This is explained by the weak but nevertheless decisive solvation of $K^+$ by interaction with the carbonyl groups of bis(2-ethylhexyl)sebacate. Because perfluorocarbons have the lowest polarity of all known compounds, it is expected that potentiometric sensors with fluorous matrixes provide the highest possible selectivities.

To test, the cation selectivity of perfluorinated solvents doped with the fluorinated tetraphenylborate 2 was determined. These solutions were supported by the porous Teflon® supports described above. For certain fluorous solvents the electrical resistance of these membranes is too high for meaningful potentiometric measurements because the anionic sites form too strong ion pairs with the tested cations. In these cases, the fluorous membranes is doped additionally with a fluorous electrolyte salt. Selectivities were measured for $Li^+$, $Na^+$, $K^+$, $Mg^{2+}$, $Ca^{2+}$, $[N(CH_2CH_3)_4^+$, $[N(CH_2CH_2CH_3)_4]^+$, and $[N(CH_2CH_2CH_2CH_3)_4]^+$ as representative ions. The selectivity measurements were performed with PFPHP (mp 215° C.) as a representative perfluorocarbon solvent without any heteroatoms, perfluoro(tripentylamine) as a perfluorocarbon with a nitrogen heteroatom, a linear perfluoropolyether (α-heptafluoropropyl-ω-pentafluoroethoxy-poly[oxy(1,1,2,2,2,3,3-hexafluoro-1,3-propanediyl)] MW 2700) and the branched 2H-perfluoror-5,8,11,14-tetramethyl-3,6,9,12,15-tetraoxaoctadecane (mp −95° C., bp 221-225° C.) as perfluorocarbons with oxygens as heteroatoms, and—for comparative reasons—a chloroparaffin and o-nitrophenyl octyl ether. The influence of the heteroatoms on the selectivity was of interest. On one hand, the electron withdrawing effect of multiple fluorine atoms reduces the nucleophilicity of perfluorinated ethers and amines, although quantitative information such as pK values for perfluorinated amines are not available form the literature. On the other hand, it may be that the sodium salt of the fluorophilic borate 2 is soluble in perfluoro(butyltetrahydrofuran) because of (presumably weak) interactions with the ether oxygen of this solvent. In view of selectivities of receptor-based ISEs of as high as 10 and more orders of magnitude, the solvation properties of plasticizers must be known.

Using fluorous liquid-membrane cation-selective electrodes doped with tetrakis[3,5-bis(perfluorohexyl)phenyl] borate salts, Bühlmann et al. have quantified interactions between inorganic monocations and perfluorotripentylamine and 2H-perfluoro-5,8,11-trimethyl-3,6,9,12-tetraoxapentadecane (*J. Am. Chem. Soc.*, 2005, 127, 16976). The amine does not undergo measurable association with any ion tested, and its form al $pK_a$ is shown to be smaller than −0.5. This is consistent with the nearly planar structure of the amine at its nitrogen center, as obtained with density functional theory calculations. This shows that perfluorotrialkylamines are promising plasticizers for fluorous membranes. The tetraether interacts very weakly with $Na^+$ and $Li^+$. Assuming 1:1 stoichiometry, formal association constants were determined to be 2.3 and 1.5 $M^{-1}$, respectively. This disproves an earlier proposition that the Lewis base character in such compounds may be non-existent, but it also confirms that perfluoropolyethers are very suitable as plasticizers for fluorous sensing membranes.

Analogous measurements of anion selectivities are performed with perfluorinated solvents doped with a fluorinated anion exchanger sites. Exemplary ions suitable for use include $F^-$, $Cl^-$, $Br^-$ $I^-$, $SCN^-$, $NO_2^-$, $NO_3^-$, sulfate, phosphate, arsenate, $ClO_4^-$, $IO_4^-$, $(B(C_6H_5)_4)^-$, $CH_3COO^-$, $CH_3(CH_2)_4COO^-$, perfluorooctanoate, and perfluorooctylsulfonate.

Perfluorinated Polymers Matrixes for Potentiometric Sensors

While a system using perfluorinated solvents supported by a porous Teflon® membrane is suitable certain purposes, it has a limited mechanical stability. In some embodiments, perfluorinated polymeric sensing membranes with higher mechanical robustness are desired. In one embodiment, the recently developed and now commercially available Teflon® AF polymers may be used as membrane matrixes. Since Teflon® AF polymers have a limited solubility in perfluorinated solvents, an electrolyte may be obtained by spin-coating a perfluorocarbon solution.

In another embodiment, the perfluoropolymer poly(perfluorobutenyl vinyl ether) may replace the Teflon® AF polymer. For example, when poly-(perfluorobutenyl vinyl ether) is plasticized with 40% or more perfluoroperhydrophenanthrene, the glass transition temperature of the resulting composition is at room temperature, making the material soft enough for many applications. In another embodiment, non-soluble electrolyte perfluoroelastomers may be doped, either by impregnation or by covalent attachment of ionic sites or receptor groups.

Soluble Polymers Matrixes Based on Teflon® AF

Teflon® AF polymers are copolymers of tetrafluorethylene and 2,2-bis(trifluoromethyl)-4,5-difluoro-1,3-dioxole. Despite the numerous oxygens in Teflon® AF polymers, there is no significant difference between the chemical stability of polytetrafluoroethylene and Teflon® AF polymers toward concentrated bases and mineral acids. Teflon® AF polymers are very suited for example, as glazings for HF reactors. As shown by Bühlmann et al. (*J. Am. Chem. Soc.*, 2005, 127, 16976) the oxygens in perfluoropolyethers similar to those of Teflon® AF are extremely weakly coordinating, making them a very suitable material for chemical sensors. Teflon® AF polymers have some of the lowest dielectric constants, ∈ known for any polymers.

The dioxole rings of Teflon® AF polymers effectively inhibit crystallization. While polytetrafluoroethylene is highly crystalline, Teflon® AF polymers are completely amorphous and therefore, optically clear. This makes these polymers attractive for optoelectronic devices, coating of sight windows and optical devices, including integrated optics, optical fibers and optical fiber claddings Unlike most other perfluoropolymers, Teflon® AF polymers are soluble in certain (perfluorinated) solvents. Importantly, the solubility is limited exclusively to a few perfluorinated solvents. The degree of solubility depends on the average chain length and on the ratio of tetrafluoroethylene and dioxole units. The solubility of Teflon® AF polymers makes it not only easy to prepare the approximately 0.2 mm thick self-supporting membranes typically used for ionophore-based membranes by solvent casting, but it also makes it easily possible to dope the perfluoromatrix with the analyte-specific ionophore, ionic sites, and other modifiers. Moreover, it also makes it possible to prepare much thinner membranes on supports by spin coating, and to impregnate porous supports with otherwise highly viscous sensing membrane components.

There must be a minimum mobility of at least one ionic species in a potentiometric ionophore-based sensing membrane, or else the electrical membrane resistance becomes too high for most electrochemical, and in particular potentiometric, measurements. Since the mobility of any small species in a polymer rises significantly above the glass transition temperature $T_g$, the $T_g$ of Teflon® AF polymers is of considerable interest. While $T_g$ falls monotonously from 350 to 80° C. as the percentage of the dioxole monomer is lowered from 100 to 20%, Teflon® AF polymers with lower dioxole contents are partially crystalline because of the presence of extended pure polytetrafluoroethylene sequences. Importantly, two Teflon® AF polymers with $T_g$ values of 160 and 250° C. have become commercially available in 1999. As an alternative to synthesizing polymers with the goal to find one with a $T_g$ below room temperature, the $T_g$ of Teflon® AF polymers may be lowered below room temperature by blending with plasticizers. The later are organic compounds of low molecular weight but high boiling points. They are admixed to polymers to make them softer and prevent cracking or breaking. As an example, plasticizers for poly(vinyl chloride), such as bis(2-ethylhexyl)phthalate and bis(2-ethylhexyl)sebacate are produced in millions of tons per year and are important bulk products in the chemical industry.

In one embodiment, the invention provides a composition comprising Teflon® AF and a plasticizer. The composition can comprise at least 1% and up to 99% plasticizer. In a more typical case, the range of plasticizer is between 10 and 90%. Perfluoropolyethers are plasticizers suitable for testing and use in connection with Teflon® AF and are commercially available under names such as Demnum, Krytox, or Fomblin Z. They have a linear or branded structure (e.g. $CF_3CF_2CF_2(OCF_2CF_2CF_2)_m OCF_2CF_3$ and $CF_3CF_2CF_2(OCF(CF_3)CF_2)_m OCHCF_3$, respectively), and have typical molecular weights ranging from 1000 to 5000 and above. Because of their oxygens, the perfluoropolyethers are much more flexible than perfluoroalkanes. This explains why perfluoroalkanes are (often viscous) liquids over very wide temperature ranges, while perfluoroalkanes have relatively high melting points. Perfluoropolyethers are used as lubricants for magnetic recording media.

Differential scanning calorimetry (DSC) is performed to determine the $T_g$ of the plasticized Teflon® AF membranes. The lack of a first order transition in DSC curves confirms the absence of crystalline regions, and a second order transition will permit the determination of the $T_g$. A plasticizer that lowers the $T_g$ sufficiently is determined and Teflon® AF membranes doped with ionophore, ionic sites, and (if necessary) fluorophilic electrolyte are used to measure potentiometric selectivities, as described above.

Alternative Perfluoroelastomer Matrixes

Perfluoroelastomers may be suitable substitutes for amorphous non-elastic perfluoropolymers, such as poly(perfluorobutenyl vinyl ether) or Teflon® AF polymers. As is the case for Teflon® AF, crystallization of linear perfluoroethylene chains in perfluoroelastomers is prevented by copolymerization with perfluorinated monomers that carry additional groups, such as a trifluoromethyl or perfluoroalkyl group. Heteroatoms such as oxygens are not present, but smaller concentrations of a third monomer permit crosslinking. Polymers of this class differ from one another mainly in the type and concentration of the crosslinkers. Commercially available products are sold under the names Kalrez, Perlast, and Chemraz. They are used mostly in o-rings, seals and packings for semiconductor wafer processing, in the oil, gas and automotive industry, and for aerospace engines and satellite. Since the primary function of these products relies on their elasticity, their Tg values are low (typically −10° C. and lower).

Plastification is performed by impregnating perfluoroelastomer disks with a perfluoro(methylcyclohexane) solution of a perfluoropolyether or PFPHP as plasticizer, an ionophore, ionic sites and (if necessary) a fluorophilic electrolyte salt. Once the elastomer is swelled with this solution, the solvent is allowed to evaporate, leaving the plasticizer, ionophore and ionic sites trapped in the perfluoroelastomer. The result should be a soft elastic material. To determine the optimum weight ratio of plasticizer and polymer, a simple assay has been developed. Several batches of polymer are exposed to solutions of different amounts of plasticizer, and the solvent is allowed to evaporate. The resulting plasticized polymer material is then rolled over a glass slide with a spatula. If the weight ratio of plasticizer and polymer is too large, the composite leaves behind a trace of plasticizer that can be readily observed under the microscope.

Receptor-Based Chemical Sensors with Perfluoropolymer Matrixes

Receptor-based ISEs are more selective than receptor free ion-exchange membranes and therefore more attractive for measurements in industrial or clinical laboratories. Fluorophilic receptors suitable for use in connection with potentiometric sensing can be synthesized and incorporated into the perfluororopolymer described above.

Proton-Selective Sensor $H^+$ receptors are readily synthesizable and provide for extraordinary selectivity. An $H^+$ selective sensor would be useful in many fields. For example, they would find application in invasive medicine and food processing, where the risk of breakage of conventional glass electrodes is unacceptable.

Figure 8:
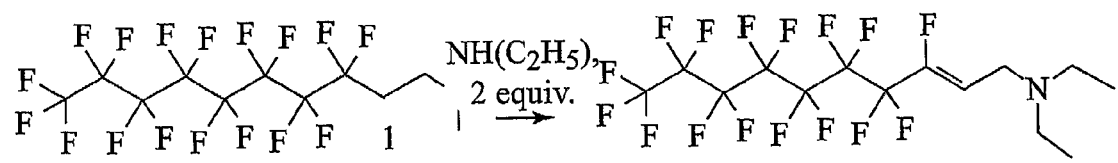
FIG. 8 illustrates the synthesis of a fluorophilic $H^+$ receptor.

One of the most selective functional receptor groups of $H^+$ is the amino group. Selectivity factors higher than $10^{10}$ have been reported. The synthesis of a fluorophilic $H^+$ receptor requires a perfluoroalkyl substituent that provides for solubility in the fluorous phase. FIG. 8 illustrates the synthesis of a fluorophilic $H^+$ receptor. An ethylene spacer between the perfluoroalkyl group and the amino group is required to realize the receptor. Without an ethylene spacer, the basicity of the ionophore would be too low for use as a $H^+$ ionophore.

Together with ionic sites and (if necessary) a fluorophilic electrolyte salt, this ionophore is incorporated into plasticized perfluoropolymers. A method including two steps is used to characterize the sensor. In one step, sensor characteristics, such as selectivity, response, time, and detection limit, are determined. In another step, the effect of lipids on the response of this sensor is assessed. Dairy products, such as cheese, are suitable for use in characterizing the sensor for use in the presence of lipids. Further, for environmental applications, changes in selectivity is determined after continuous environmental exposure. For example, to characterize a sensor for an environmental application, the sensor membrane is be exposed to flowing river water or to ground water. For comparison, PVC membranes plasticized with o-nitrophenyl octyl ether are similarly exposed.

Chloride-Selective Sensor

Figure 9:
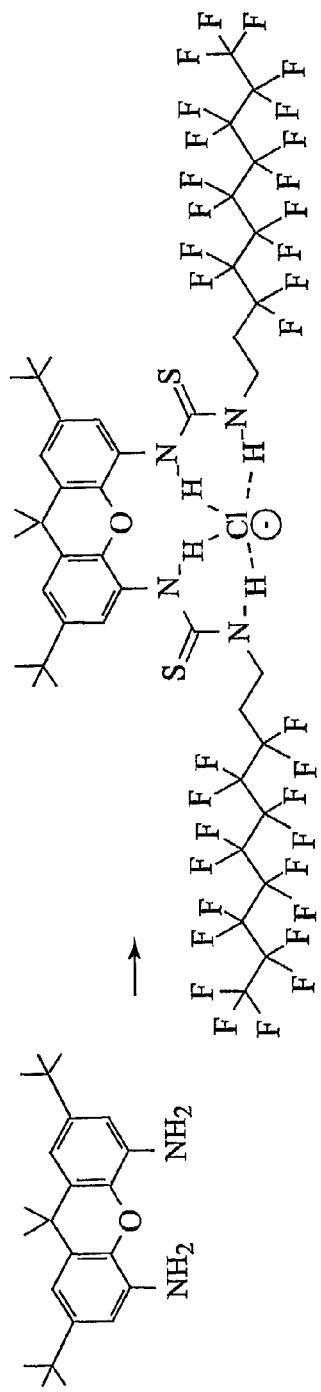
FIG. 9 illustrates the synthesis of a chloride receptor.

A $Cl^-$ selective sensor is suitable for use in connection with clinical and environmental applications. FIG. 9 illustrates the synthesis of a chloride receptor. In the central synthesis step, a diamine is reacted to a hydrogen-bonding ionophore by reaction with two equivalents of a perfluoroalkylethyl isothiocyanate. Without the $CH_2CH_2$ spacer between the nitrogen atom and perfluoroalkyl substituents, the electron-with-drawing fluorines would lower the pK of the thiourea groups of the resulting receptor. The ionophore would not be useful in alkaline solutions due to deprotonation.

Sensors based on this chloride receptor are characterized by methods described above for the $H^+$ selective sensor. An alternative approach using a fluorinated Mn (III) porphyrin may be used. The introduction of eight perfluorohexyl groups provides a fluorophilic porphyrin.

Creatininium-Selective Sensor

The creatininium selectivity of receptor-free ISEs toward the major cations of urine ($K^+$, $Na^+$) is high enough to make a creatininium-selective sensor suitable for use in connection with a sensor designed for use in clinical measurements. The problem with the loss of selectivity encountered in the extraction of electrically neutral lipids from urine samples in chloroparaffin-plasticized sensor matrixes (as described above) is reduced through the use of a fluorous sensor matrix. Development of a creatininium-selective sensors includes measurement of the creatininium $K^+$ and $Na^+$ selectivities of a receptor-free fluorous cation exchanger electrode and testing of interference from neutral lipids. Exemplary lipids suitable of use in connection with testing the creatininium-selective sensor include p-cresol, cholesterol, phosphatidylserine, phosphatidylethanolamine, and taurocholic, cholic and octanoic acid.

Figure 10:
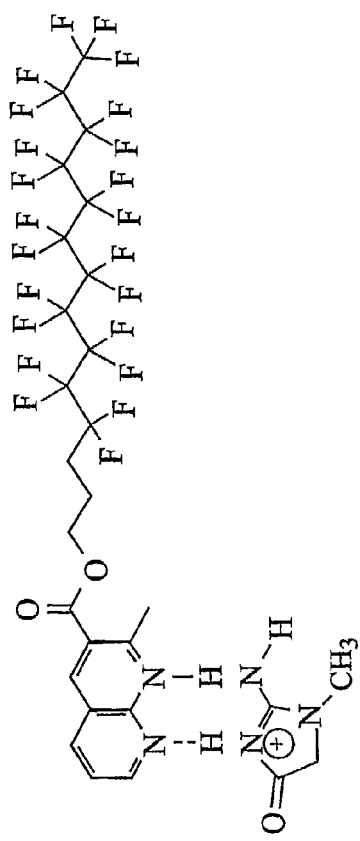
FIG. 10 illustrates the structure of a receptor for protonated creatinine.

For electrodes with particularly high selectivity, the cation-exchanger electrodes can be doped with the 1,8-naphthyridine receptor as its creatininium complex. FIG. 10 illustrates the structure of a 1,8-naphthyridine receptor. The incorporation of both hydrogen bond donors and acceptors into the same receptor is avoided. While receptors with hydrogen bond donors and acceptors can form more stable 1:1 creatininium complexes than receptors with hydrogen bond donors or acceptors only, self-association of the receptor in a sensing membrane eliminates the advantage of receptors with both hydrogen bond donors and acceptors. Also, hydrogen bond donating groups of a receptor cannot interact with the carbonyl group of creatininium, which is a very weak hydrogen bond donor. An ionophore that forms an additional (third) hydrogen bond to the second hydrogen of the $NH_2$ group would be more effective, but may not be necessary to achieve sufficiently high selectivity. It should be noted that the 1,8-naphthyridine-based receptor requires only one step synthesis, while an ionophore with 3 hydrogen bond acceptor sites requires a synthesis with at least five steps.

Example 2

Fluorous Bulk Membranes for Potentiometric Sensors with Wide Selectivity Ranges

Observation of Exceptionally Strong Ion Pair Formation

Figure 11:
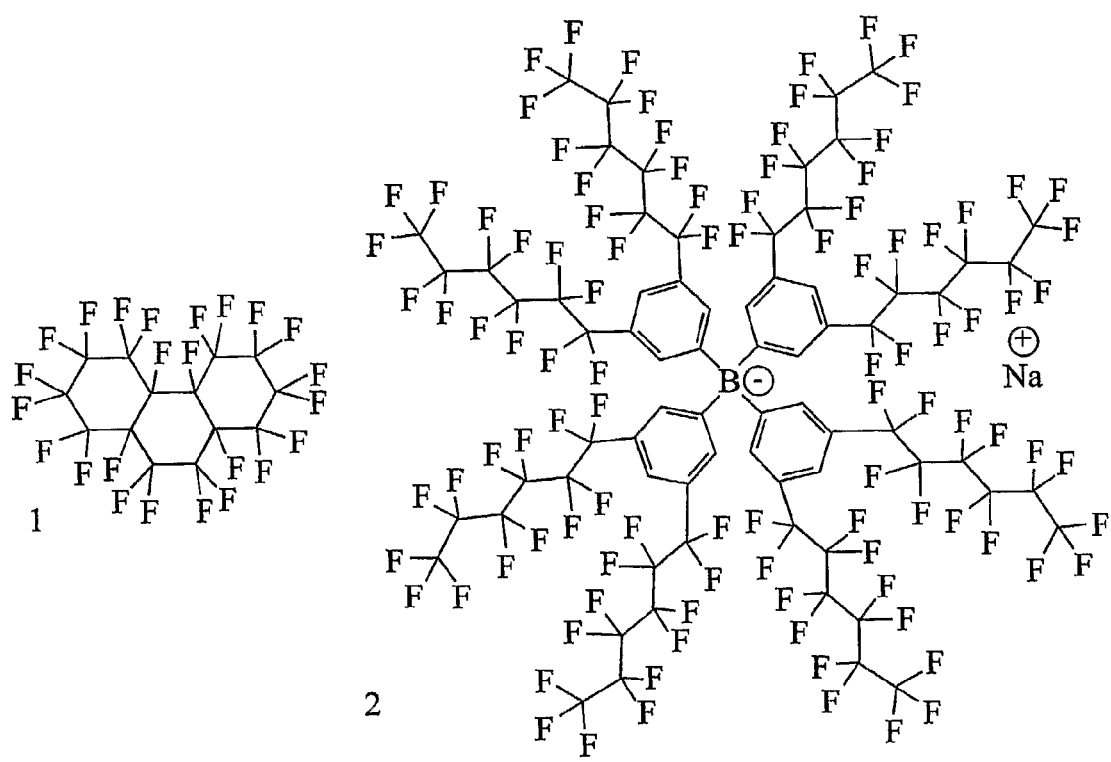
FIG. 11 illustrates the structure of perfluoroperhydrophenanthrene (1) and the structure of sodium tetrakis[3,5-bis(perfluorohexyl)phenyl]borate (2).

Only a very small number of salts with solubility in fluorous solvents have been reported in the literature. FIG. 11 illustrates the structure of perfluoroperhydrophenanthrene (1) and the structure of sodium tetrakis[3,5-bis(perfluorohexyl)phenyl]borate (2). Solutions of a fluorophilic salt in perfluoroperhydrophenanthrene, 1 (bp 215° C.), were used as fluorous cation-selective potentiometric sensing phases. Highly hydrophobic tetraphenylborate salts commonly used in ISEs were found to be insufficiently soluble in fluorous phases. Not even lithium perfluoroterraphenylborate and potassium tetrakis[3,5-bis(trifluoromethyl)phenyl]borate dissolved appreciably in fluorous solvents. However, sodium tetrakis[3,5-bis(perfluorohexyl)phenyl]borate, a colorless salt, 2, was synthesized in two steps from 1,3,5-tribromobenzene and was found to have a solubility in 1 of 1.4 mM.

The eight perfluorohexyl groups of 2 result in a fluorine content of 67.5% (w/w) and cause the high solubility of this salt in 1, which itself has a fluorine content of 73.1%. In view of the exceptionally low polarity of fluorous solvents a high tendency of 2 to form ion pairs was expected. To explore this possibility, the concentration dependence of the molar conductivity of 2 was determined in an electrochemical cell. For this purpose, porous Teflon® filters were impregnated with solutions of 2 in 1. Since Teflon® is not swelled by these solutions, it is an inert support for the liquid fluorous phase. The fluorous membranes prepared in this way were mounted into an electrode body custom-made from poly(chlorotrifluoroethylene), and this body was equipped with an inner Ag/AgCl reference and internally filled with a 1 mM NaCl solution. An electrochemical cell was obtained by immersion of the thus fabricated electrode and an external reference electrode of the double junction type (saturated KCl as inner solutions and 1 M LiOAc as bridge electrolyte) into a NaCl sample solution. A plot of the EMF of this cell as a function logarithm of the $Na^+$ concentration shows a Nernstian response slope, confirming that the $Na^+$ remains in the fluorous membrane. The resistance of the fluorous membranes were then determined with the known shunt method. Ion pair formation constants, $K_{ip}$ ($M^{-1}$), were obtained form the concentration dependence of the membrane resistance. Molar conductivities, $\Lambda$, calculated from the measured resistances, were fitted with $\Lambda = \lambda_o K_{ip}^{-1/2} (c^{-1/2} + 2K_1 c^{1/2}/3)$, where c is the total concentration of the fluorophilic salt, $\lambda_o$ is its limiting molar conductivity, and $K_1$ is the triple ion formation constant. To obtain $K_{ip}$ values for other cations, membranes were equilibrated with solutions of the chloride salt of different cations of interest. Successful ion exchange was confirmed by Nernstian responses of thus conditioned membranes to the new cations.

FIG. 12 shows Table 1 which provides ion pair formation constants in perfluoroperhydrophenanthrene containing tetrakis[3,5-bis(perfluorohexyl)-phenyl]borate and various cations. The log $K_{ip}$ values fall into the relatively narrow range of 20.11 to 20.73, excluding the possibility of very specific cation-anion interactions. These are the first reported $K_{ip}$ values for ion pair formation in a fluorous solvent. These $K_{ip}$ values exceed previously reported ones by at least 5 orders of magnitude. For example, for tetraoctylammonium chloride in 98.2 toluene-nitrobenzene, a log $K_{ip}$ of 14.9 was determined, and for tetrakis-(decyl)ammonium tetraphenylborate in cyclohexane, a log $K_{ip}$ of 14.2 was found. Notably, the $K_{ip}$ values reported here also considerably exceed constants reported for ion pair formation in $\alpha,\alpha,\alpha$-trifluorotoluene, which takes an intermediate role between hydrocarbons and fluorous solvents, since it is miscible with both. While $\alpha,\alpha,\alpha$-trifluorotoluene is, to date, the "most fluorous" solvent for which electrochemistry has been reported, its dielectric constant, $\in$, of 9.2 is relatively high and the log $K_{ip}$ of 5.4 for tetrabutyl-ammonium tetrafluoroborate is rather low.

In view of chemical sensing, the potentiometric selectivities of the electrodes described above are of particular interest. FIG. 13 shows Table 2 which provides potentiometrically determined logarithmic selectivity coefficients, log $K^{pot}_{Cs,J}$, referenced to $Cs^+$ for fluorous, nonfluorous ion exchanger, and ionophore-based ISE membranes. Selectivity coefficients of fluorous and conventional receptor-free ISE membranes are compared. The $Cs^+$ ion serves as the common reference point.

While the selectivities of the fluorous membranes span a remarkably wide range of more than 16 orders of magnitude, the selectivity range for membranes prepared for poly(vinyl chloride), the plasticizer chloroparaffin, and the lipophilic anion tetrakis[3,5-bis(trifluoromethyl)phenyl]borate (KFPB, membrane type II) is limited to only 8 orders of magnitude. Notably, the perfluorohexyl-substituted anion of 2 does not appear to interact with appreciable specificity to alkali metal ions, as a comparison of the selectivities of type III and type IV membranes shows. Both types were prepared with o-nitrophenyl octyl ether (oNPOE) as plasticizer, but the latter contained potassium tetrakis(4-chlorophenyl)borate (KClPB) instead of 2 as the lipophilic anion. Nevertheless, their selectivities do not differ substantially.

Surprisingly, the selectivities of fluorous membranes not only compare well with those of receptor-free membranes but also are in the range of those of ionophore-based $Cs^+$ selective electrodes (see FIG. 13). Since the high selectivities of the fluorous membranes are the result of the low extent of solvation of interfering ions, we expect that similarly receptor-based fluorous membranes will be much more selective than corresponding nonfluorous ones.

These results show that potentiometry with fluorous sensing membranes exhibits extraordinarily high selectivities. The exceptionally low polarity of these sensing membranes is evidenced by unprecedented strong ion pair formation, and the low solubility of lipids in fluorous phases is of great promise in view of the reduction of biofouling.

Conductimetric and Potentiometric Measurements

Sample solutions were made with deionized and charcoal-treated water ($\geq 18.2$ M$\Omega$ cm specific resistance) obtained with a Milli-Q PLUS reagent-grade water system (Millipore, Bedford, Mass.). Double-junction sleeve-type Ag/AgCl reference electrodes (DX200, Mettler Toledo, Switzerland) and EMF 16 16-Channel Data Acquisition System potentiometers (Lawson Labs, Malvern, Pa.) were used for all potentiometric and conductimetric measurements. Mitex™ membrane filters made of pure Teflon® (13 mm diameter, 10 μm pore size, 125 μm thick) were obtained from Millipore.

1-Bromo-3,5-bis(perfluorohexyl)benzene (3)

Figure 14:
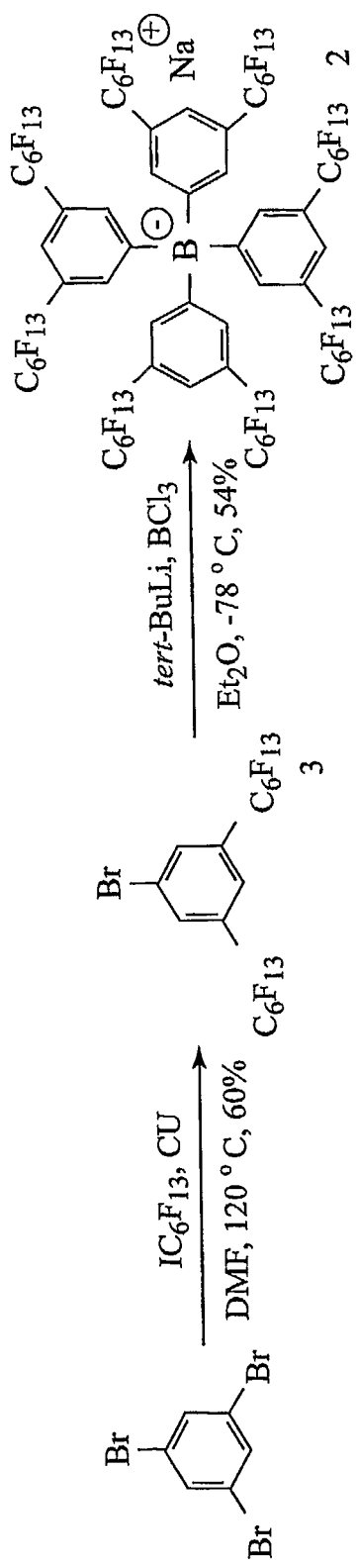
FIG. 14 illustrates the synthesis of sodium tetrakis[3,5-bis(perfluorohexyl)phenyl]borate (2).

Compound 3 in FIG. 14 was prepared with 60% yield using a literature procedure describing the synthesis of 1-bromo-3,5-bis(perfluorooctyl)benzene.

Sodium tetrakis[3,5-bis(perfluorohexyl)phenyl]borate (2)

FIG. 14 illustrates the synthesis of sodium tetrakis[3,5-bis(perfluorohexyl)phenyl]borate (2). A raw product of 2 was prepared. The greenish-brown oil, which was previously reported to be the pure product, was further purified by thorough drying under vacuum and recrystallization from perfluorohexanes to give the product as colorless crystals. $^1$H NMR (500 MHz, acetone-d$_6$, δ): 7.72 (s, 8H), 7.59 (s, 4H). MS m/z (relative intensity): 2861.0 (20.6%), 2862.0 (100%), 2863.0 (71.6%), 2864.0 (25.2%), 2865.0 (6.5%). Anal. Cald. for $C_{72}H_{12}BF_{104}Na$: C, 29.96; H, 0.42; B, 0.37. Found: C, 30.05; H, 0.60; B, 0.87. Boron analysis was performed by ICP-AES (Quantitative Technologies Inc., Whitehouse, N.J.).

Potentiometric Measurements

Three types of polymeric membranes were fabricated and characterized simultaneously with the fluorous liquid-phase membranes. Each polymeric membrane contained plasticizer and poly(vinyl chloride) in a 2:1 ratio. The lipophilic salts potassium tetrakis[3,5-bis(trifluoromethyl)phenyl]borate (KFPB) or potassium tetrakis(4-chlorophenyl)borate (KClPB) were added to the o-NPOE (0.2%, w/w) or chloroparaffin (0.3%, w/w) membranes to provide for ionic sites.

Figure 15:
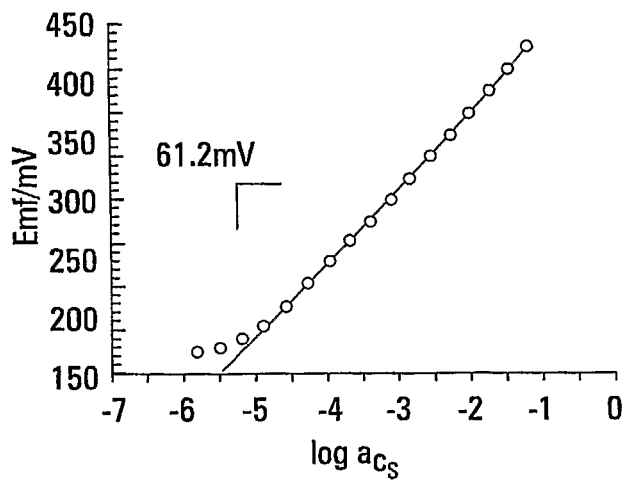
FIG. 15 shows a $Cs^+$ calibration curve acquired with supported perfluoroperhydrophenanthrene phase containing 1.4 mM cesium tetrakis[3,5-bis(perfluorohexyl)-phenyl]borate.

The fluorous liquid-phase membranes were prepared by transferring 12 μL of a saturated solution of 2 in perfluoroperhydrophenanthrene, 1, onto the surface of a porous Teflon® filter, into which this solution was quickly absorbed. Each filter soaked with solution of 2 in 1 was then placed in a custom electrode body and mechanically sealed around the perimeter, leaving an exposed region 8.3 mm in diameter. FIG. 15 shows a typical calibration curve of one of these fluorous electrodes. More specifically, FIG. 15 shows a Cs$^+$ calibration curve acquired with supported perfluoroperhydrophenanthrene phase containing 1.4 mM cesium tetrakis[3,5-bis(perfluorohexyl)-phenyl]borate.

Perfluoroperhydrophenanthrene, 1, was chosen because it has a sufficiently high boiling point and low pour point (–20° C.) to make it useful as a fluorous liquid phase and possibly as a fluorous plasticizer for fluorous polymeric membranes. Linear perfluorinated alkanes have ranges between their melting and boiling points that are too narrow to be useful as fluorous phases, and branched perfluorinated alkanes are not readily available.

Figure 16:
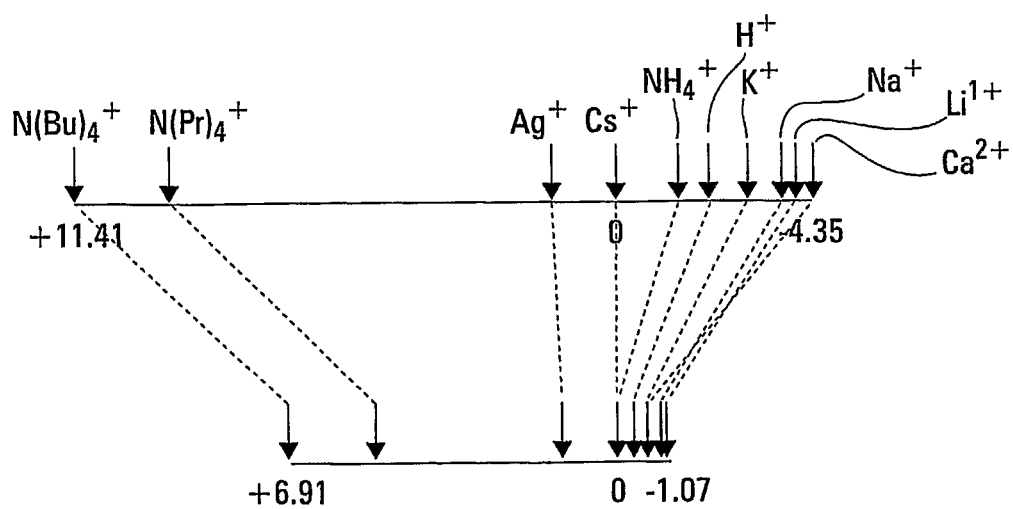
FIG. 16 shows a selectivity diagram comparing the logarithmic selectivity coefficients of several cations referenced to $Cs^+$ between (a) a fluorous membrane, and (b) a chloroparaffin/PVC membrane.
Figures 17, 18:
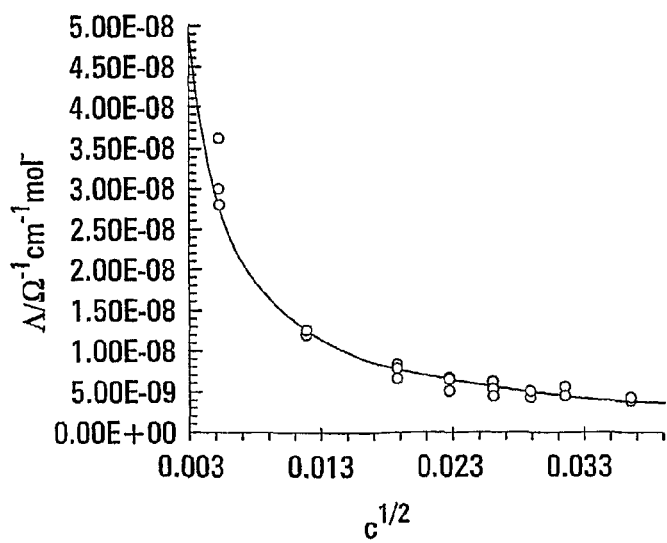
FIG. 17 shows potentiometrically determined logarithmic selectivity coefficients, log $K^{pot}_{Cs,J}$, referenced to $Cs^+$ for fluorous ion exchanger, nonfluorous ion exchanger, and ionophore based ISE membranes.
FIG. 18 shows molar conductivity, A, plotted as a function of the square root of the concentration of the $Cs^+$ salt of 2, as shown in FIG. 14, with a Fuoss-Kraus fit.

Selectivity coefficients were determined by the fixed interference method for Li$^+$, Na$^+$, K$^+$, NH$_4^+$, and H$^+$, while the separate solution method was employed for Ca$^{2+}$, Ag$^+$, (CH$_3$CH$_2$CH$_2$)$_4$N$^+$, and (CH$_3$CH$_2$CH$_2$CH$_2$)$_4$N$^+$. Nernstian responses were confirmed for all ions in the range where selectivities were tested. Activity coefficients were calculated according to a two-parameter Debye-Hückel approximation. FIG. 16 shows a selectivity diagram comparing the logarithmic selectivity coefficients of several cations referenced to Cs$^+$ between (a) a fluorous membrane, and (b) a chloroparaffin/PVC membrane. In general, FIG. 17 shows a complete list of selectivity measurements made with the electrodes described in this study. More specifically, FIG. 17 shows potentiometrically determined logarithmic selectivity coefficients, log $K^{pot}_{Cs,J}$, referenced to Cs$^+$ for fluorous, nonfluorous ion exchanger, and ionophore based ISE membranes. For these selectivity measurements, Cs$^+$ was considered as the primary ion, and the inner filling solution of the ISE contained 1 mM CsCl.

Conductimetric Measurements

Due to the high resistance of solutions of 2 in perfluoroperhydrophenanthrene, conductivity cells with an acceptable cell constant and sample volume are not commercially available. Instead, a conductivity cell with a fluorous liquid phase supported by a porous Teflon® filter (cell constant=0.034 cm$^{-1}$), as described above for the potentiometric measurements, was used. All conductivities were determined with a potentiometer (input impedance 10 TΩ) using the method of potential reduction by a known shunt.

The fluorous, supported liquid-phase conductivity cells were made by transferring 12 μL of a solution of 2 in perfluoroperhydrophenanthrene, 1, onto the surface of a Teflon® filter, into which it was quickly absorbed. These membranes were then allowed to equilibrate with 10 mL of a 100 mM solution of a chloride salt of the primary ion for 1.5 to 2.5 h.

They were then placed in an electrode body of the same type used for the potentiometric measurements and immersed in a 100 mM solution of the primary ion chloride. The total resistance of the electrochemical cell without the fluorous supported liquid-phase membranes is negligible since it is more than six orders of magnitude smaller than the resistance of the fluorous membranes. Shunts used for these measurements had resistances in the range of 1.0-10 GΩ.

In order to ensure complete conditioning of the membranes, the time required for equilibration of membranes upon contact with cation solutions was determined by two independent methods. When membranes containing 2 were exposed in a Petri dish to 10 mM CsCl or NaCl solutions (one side of the membrane contacting the solution) and allowed to equilibrate with those solutions for 1-hour increments of time up to 5 hours, membrane resistances approached a final value within one hour. No significant difference between resistances measured after 1, 2, 3, 4, and 5 hours was observed. These observations suggest that these thin fluorous phases equilibrate with the solutions within less than one hour. This conclusion is consistent with potentiometric results. When membranes containing 2 were placed into electrode bodies of the same type used for potentiometric measurements and immersed into 100 mM CsCl solutions, stabilization of the membrane potentials required less than 25 min.

The relation between molar conductivity and fluorous salt concentration in 1 can be fitted with the Fuoss-Kraus theory, $\Lambda=(\lambda_o/c^{1/2}K_{ip}^{1/2})+(\lambda_{o,t}c^{1/2}K_t/K_{ip}^{1/2})$, where $\Lambda$ is the molar conductivity, c is the salt concentration, $\lambda_o$ and $\lambda_{o,t}$ are the limiting molar conductivities for free and triple ions, respectively, $K_{ip}$ is the ion pair formation constant, and $K_t$ is the triple ion formation constant. $\lambda_{o,t}$ is commonly approximated with $2\lambda_o/3$.

More complex theory can compensate for free ion activities, changes in viscosity with the total salt concentration, and formation of quadrupoles consisting of two cations and two anions. However, only a small range of salt concentrations was available experimentally for conductivity measurements. The relatively low solubility of 2 in 1 limits the upper range of salt concentrations available for conductivity measurement, and the extremely high resistance of the perfluoroperhydrophenanthrene solutions limits the accuracy of conductivity measurements at low salt concentrations. While the small range of salt concentrations allowed accurate measurements of $K_{ip}$, the constants for the formation of triple ions (and quadrupoles, when fitting with more complex models) are associated with larger errors. Importantly, the more complex models show that taking into account the formation of any complexes larger than ion pairs does not change the estimated values of $K_{ip}$ significantly.

FIG. 18 shows molar conductivity, $\Lambda$, plotted as a function of the square root of the concentration of the Cs$^+$ salt of 2, as shown in FIG. 14, with a Fuoss-Kraus fit. And as this fit shows, values for the limiting molar conductivities, $\lambda_o$, are required to determine $K_{ip}$ from fits as illustrated by FIG. 18. Due to the strong ion pair formation in 1 and the limited salt concentration range for accurate conductivity measurement, the direct measurement of limiting molar conductivities is not feasible.

Therefore, limiting ionic molar conductivities were determined by the Stokes-Einstein approximation, which is known to have greater accuracy in solvents of lower dielectric constant: $\lambda_o^i = (z_i^2 F^2)/(6N_A \pi \eta r_i)$, where F is the Faraday constant, $N_A$ is Avogadro's constant, r is the crystallographic ion radius, and η is the viscosity of the solvent (25° C., 28.4 cP). This approximation was used previously for the determination of ion pair formation constants in media of very low dielectric constants. The limiting molar conductivity of the salt is given by $\lambda_o = \lambda_o^+ + \lambda_o^-$ for a 1:1 electrolyte. Crystallographic ionic radii from the literature 11 were used for cations, and the radius of the fluorophilic borate was approximated to be 10 pm. Even a comparatively large error in the radius of the borate would not affect the calculated ion pair formation constants significantly because the conductivities are dominated by the smaller, more mobile cations.

Relevance to Biofouling

As described above, the lipophilic cholic acid at a concentration of $10^{-3.5}$ M has been shown to cause a drift of 55-60 mV in conventional PVC-based electrodes (Bühlmann et al., Anal. Chem. 2001, 73, 3199). Supported fluorous membranes containing 1.4 mM of sodium tetrakis[3,5-bis(perfluorohexyl)phenyl]borate salt and 10 mM of the electrolyte salt methyl-tris(perfluorooctylpropylammonium)tetrakis[3,5-bis (perfluorohexyl)phenyl]borate (prepared as described in Boswell, P. G.; Lugert, E. C.; Rábai, J.; Amin, E. A., Bühlmann, P., J. Am. Chem. Soc., 2005, 127, 16976) in perfluoroperhydrophenanthrene immersed into pH buffered KCl solutions (100 mM sodium phosphate buffer, pH 7) did not exhibit any drift over at least 4 hours when $10^{-3.5}$ M cholic acid was added to the KCl solutions. This demonstrates the enhanced properties of fluorous membranes towards lipophilic constituents, as they are contained in biological samples such as blood or urine. Fluorous membranes of the same composition were also exposed to aqueous buffered solutions of $10^{-3.5}$ M cholic acid or $10^{-3.5}$ M octanoic acid, and the fluorous membranes were subsequently analyzed by $^1$H NMR spectroscopy. In neither case could a detectable amount of the acid be found in the $^1$H NMR spectra, showing that these hydrophobic compounds are not extracted to any significant amount into the fluorous membranes.

Example 3

Anion Exchanger Electrode

Figure 19:
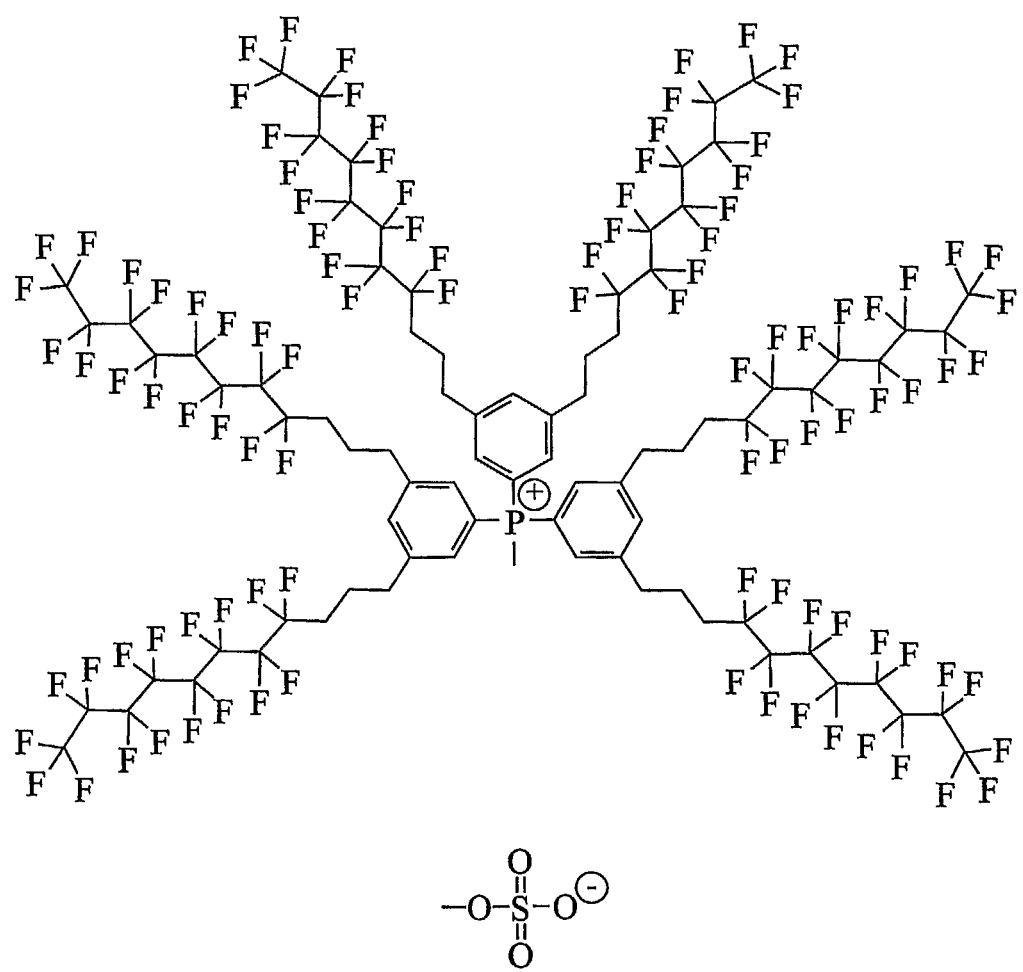
FIG. 19 illustrates the structure of the fluorophilic cation methyl sulfate salt of the tris(3,5-bis(1H,1H,2H,2H,3H,3H-perfluoroundecyl)phenyl)methyl)-phosphonium methyl sulfate cation.

As described above, the chemical sensor of the invention preferably includes in the fluorous phase the salt of a fluorous ion that is soluble therein. The fluorous ion is typically a fairly large organic species and can be an anion (negatively charged) or a cation (positively charged). As an example of a fluorophilic cation, we have prepared the methylsulfate salt of the tris[3,5-bis(1H,1H,2H,2H,3H,3H-perfluoroundecyl)phenyl] (methyl)phosphonium methyl sulfate cation. FIG. 19 illustrates the structure of the fluorophilic cation methylsulfate salt of the tris(3,5-bis(1H,1H,2H,2H,3H,3H-perfluoroundecyl)phenyl)methyl)phosphonium methyl sulfate cation.

This salt was prepared as follows: 1,3,5-Tribromobenzene was diformylated by formation of the aryldilithium reagent with tert-butyl lithium at −78° C. in diethyl ether, followed by addition of dimethyl formamide. The 3,5-diformylbromobenzene was then dialkylated in 1,4-dioxane at 95° C. for 20 hours using the Wittig reagent formed from triphenylphosphine and 1-iodo-1H,1H,2H,2H-perfluorodecane. After hydrogenation of the resulting double bonds in an 800 psi hydrogen atmosphere in the presence of a 5% Rh/C catalyst for 40 hours, an organolithium reagent was used to form 3,5-di(1H, 1H,2H,2H,3H,3H-perfluoroundecyl)phenyllithium in diethyl ether at room temperature, which was then used to triarylate PCl₃. Methylation of the resulting phosphine with dimethylsulfate was accomplished in a benzotrifluoride solution heated to 105° C. for 20 hours. Final purification yielded tris[3,5-bis(1H, 1H,2H,2H,3H,3H-perfluoroundecyl)phenyl] (methyl)phosphonium methyl sulfate. A porous Teflon® membrane was impregnated with a 14 mM solution of this phosphosphonium salt in perfluoroperhydrophenanthrene, as described above for the fluorophilic tetraphenylborate salt. This impregnated porous Teflon® membrane was incorporated into an electrode body, as described above, the electrode was inserted into KCl solutions of variable concentration, and the potential was measured. The thus obtained potentiometric response of this anion exchanger electrode was Nemstian in the range of 0.1 M to 0.0001 M. This shows that these electrodes can be used as anion-selective sensors.

The KCl exposure of the above described membrane doped with tris[3,5-bis(1H, 1H,2H,2H,3H,3H-perfluoroundecyl)phenyl](methyl)phosphonium methyl sulfate salt resulted in anion exchange, effectively creating a methyl-tris[3,5-bis (perfluorooctylpropyl)-phenyl]phosphonium chloride doped membrane. In the same way, chloride ions can be replaced by other hydrophilic anions, and the thus reconditioned sensor will respond to those other anions.

The methyl-tris[3,5-bis(perfluorooctylpropyl)phenyl] phosphonium cation could also be replaced by another fluorophilic phosphonium salt with a cation of the type $PR_1R_2R_3R^+$, where $R_1$, $R_2$, $R_3$, or $R_4$ are aryl or alkyl groups substituted with perfluoroalkyl groups that serve the only purpose of making the salt of $PR_1R_2R_3R_4^+$ soluble in the fluorous membrane. Alternatively, the methyl-tris[3,5-bis-(perfluorooctylpropyl)phenyl]phosphonium cation could also be replaced by another fluorophilic ammonium salt with a cation of the type $NR_1R_2R_3R_4^+$, where $R_1$, $R_2$, $R_3$, or $R_4$ are aryl or alkyl groups substituted with perfluoroalkyl groups that serve the only purpose of malting the salt of $NR_1R_2R_3R_4^+$ soluble in the fluorous membrane. In an alternative embodiment, the phosphonium cation could be covalent attached to the perfluoropolymer matrix.

Example 4

Example Receptor-Based Sensor

The chemical selectivity of the chemical sensors of the invention preferably arises from a receptor molecule or group that selectively binds non-covalently or covalently to the analyte of interest. A receptor molecule that is included in a chemical sensor of the invention is typically highly fluorinated so that it is soluble in the fluorous membrane matrix. For example, a proton selective electrode was used in an electrode body equipped with a porous membrane impregnated with a solution of 2.8 mM of the receptor tris(perfluorooctylpropylamine (prepared as described in Rocaboy, C.; Bauer, W.; Gladysz, J. A. Eur. J. Org. Chem. 2000, 14, 2621) and 1.4 mM sodium tetrakis[3,5-bis(perfluorohexyl)phenyl] borate (prepared as described in Boswell, P. G.; Bühlmann, P. J. Am. Chem. Soc. 2005, 127, 8958) in perfluoroperhydrophenanthrene. The resulting electrode responded Nernstian in the pH range of 3 to 10. The selectivity of this electrode for protons over sodium cations was determined to be 1 to $10^{-10.8}$, demonstrating an excellent selectivity.

Applications for Embodiments Described in Example 1, Example 2, Example 3, and Example 4

Medicine

Figure 20A:
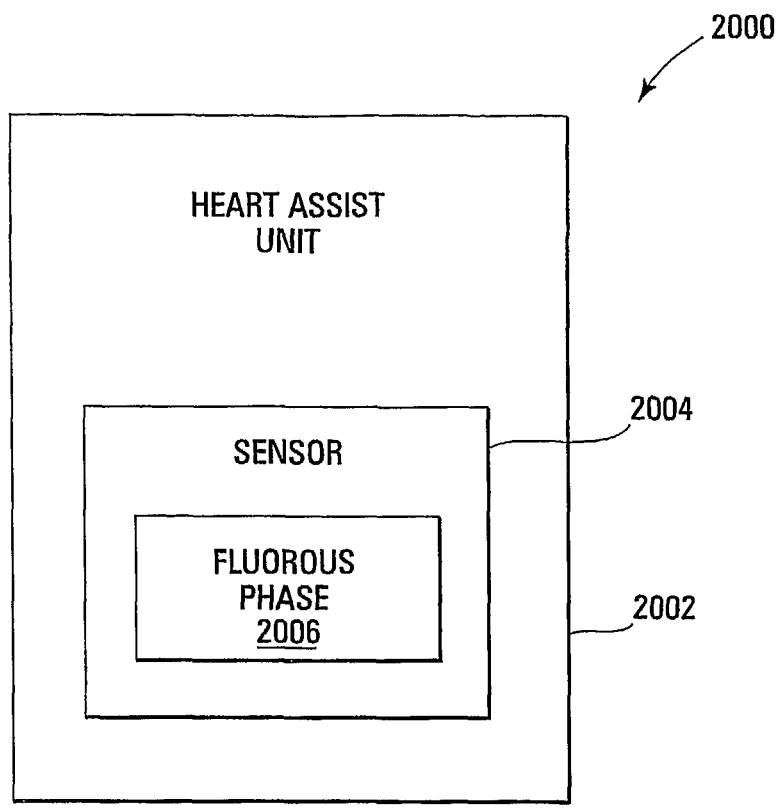
FIG. 20(a) is a block diagram of an apparatus including a heart assist unit and a sensor in accordance with some embodiments of the invention.

Fluorous phase sensors can be employed to solve problems in the field of medicine. FIG. 20(a) is a block diagram of an apparatus 2000 including a heart assist unit 2002 and a sensor 2004 in accordance with some embodiments of the invention. The heart assist unit 2002 is not limited to a particular type of heart assist unit. Exemplary heart assist units suitable for use in connection with the apparatus 2000 include defibrillators and pacemakers. A pacemaker provides a signal to a heart to regulate contraction of the heart muscle. A defibrillator provides an electrical signal to the heart to restart the heart. The sensor 2004 includes a fluorous sensing phase 2006. The fluorous sensing phase 2006 permits the sensor to detect target materials, such as an analyte, in fluids, such as liquids or gases. In some embodiments, the fluorous sensing phase 2006 is included in a matrix or substrate. Exemplary substrate materials suitable for use in connection with the fabrication of the sensor 2004 include polymers and polymers embedded in semiconductors.

Figure 20B:
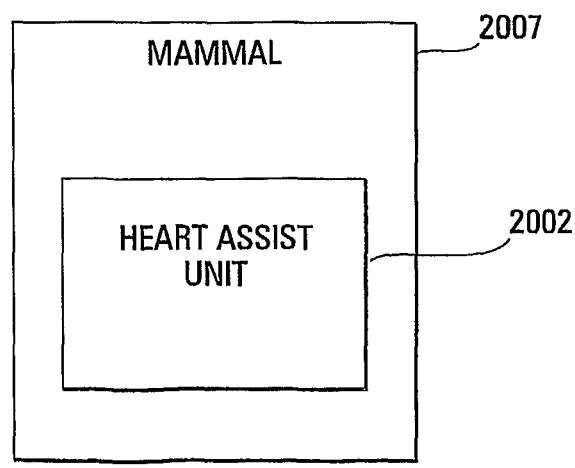
FIG. 20(b) shows a block diagram of the heart assist unit shown in FIG. 20(a) implanted in a mammal.

In operation, the sensor 2004 receives a fluid, detects a target material and provides a signal to the heart assist unit 2002 to signal detection of the target material. In some embodiments, the heart assist unit is implanted in an animal, such as a mammal. Exemplary mammals suitable for use in connection with implantation of the sensor 2004 include humans, dogs, horses, cats, dolphins, and chimpanzees. FIG. 20(b) shows a block diagram of the heart assist unit 2002 implanted in a mammal 2007.

Figure 20C:
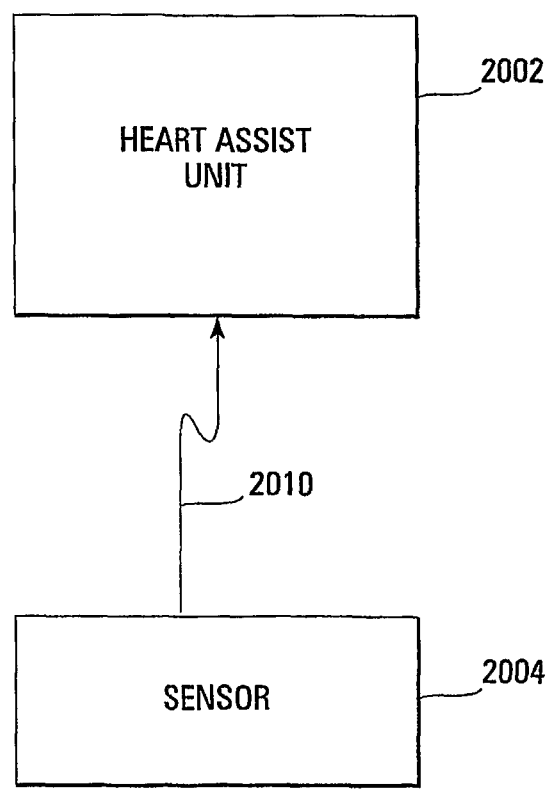
FIG. 20(c) shows a block diagram of the heart assist unit, shown in FIG. 20(a) separated from the sensor, shown in FIG.

In some embodiments, the sensor 2004 is physically separated from the heart assist unit 2002 and only communicates with the heart assist unit 2002 by transmitting a signal, for example with an electromagnetic wave, to the heart assist unit 2002. FIG. 20(c) shows a block diagram of the heart assist unit 2002 separated from the sensor 2004 with the sensor 2004 communicating with the heart assist unit 2002 by transmitting a signal by an electromagnetic wave 2010.

In alternative embodiments, the sensor with the fluorous membrane may be employed to monitor analytes in the animal or human body and alert the user, medical personnel, or a monitoring center when the concentration of the monitored analyte has gone beyond normal values. Such a sensor would typically be particularly useful in cases of sudden acute diseases, such as heart failure, stroke, or acute kidney failure.

Food Processing

Fluorous phase sensors can be employed to solve problems in the food processing industry. FIG. 21 shows a block diagram of an apparatus 2100 including a food processing unit 2102 and a sensor 2104 to generate a signal 2106 to control the food processing unit 2102 in accordance with some embodiments. The food processing unit 2102 is not limited to a particular type of food processing unit. Exemplary food processing units suitable for use in connection with the apparatus 2100 include alcoholic beverage manufacturing factories, such as factories that manufacture beer, wine, and vodka, and non-alcoholic beverage manufacturing factories, such as factories that manufacture milk, soft drinks, and sports drinks, and non-beverage factories, such as factories that manufacture cheese. The food processing unit 2102 is configured to process a particular type of food.

In operation, the sensor 2104 receives a food stream 2108 having an analyte. The sensor 2104 includes a fluorous sensing phase that allows the sensor 2104 to detect or sense the analyte in the food stream 2108. The analyte enters the sensor 2104 selectively in comparison with other components of the beverage stream. After detecting the analyte, the sensor 2104 provides the signal 2106 to the food processing unit 2102. In some embodiments, the sensor 2104 detects an increase in the level of an analyte and provides that information to the food processing unit 2102. In other embodiments, the sensor 2104 detects a decrease in the level of an analyte and provides that information to the food processing unit 2102.

The availability of clear perfluoropolymers with high tensile strength also suggests the feasibility of chemically sensitive optical fibers that are directly incorporated into solidified toxic wastes or civil structures such as bridges, roads, dams or tall buildings. These embedded fibers may be used to monitor the integrity of the structures in which they are embedded. The travel time of the optical signal, such as a signal produced by an optical source, such as a laser, can be used to determine whether the chemical environment along an optical fiber has changed. For example, a change in the pH of cement could be detected by the change in travel time of an optical pulse in an optical fiber embedded in the cement. In some environments, a change indicates an increased possibility of structural failure. Further, perfluoropolymers are stable in corrosive environments and therefore may be included in sensor networks embedded in the Earth to monitor and predict volcanic eruptions and earthquakes by detecting chemical changes in groundwater.

Optically Transmissive Medium

When included in an optically transmissive medium, a fluorous sensing phase can provide optical detection of a target material. FIG. 22 is an illustration of an apparatus 2200 including an optically transmissive medium 2202 including a fluorous sensing phase 2204. The optically transmissive medium 2202 is not limited to a particular medium. Any medium capable of transmitting electromagnetic radiation is suitable for use in connection with the apparatus 2200. In some embodiments, the optically transmissive medium transmits electromagnetic radiation in the ultraviolet and visible region of the electromagnetic spectrum. In other embodiments, the optically transmissive medium transmits electromagnetic radiation in the infrared region of the electromagnetic spectrum. In still other embodiments, the optically transmissive medium transmits electromagnetic radiation in the x-ray region of the electromagnetic spectrum. The fluorous sensing phase 2204 is included in the optically transmissive medium 2202. In some embodiments, the optically transmissive medium includes a fiber optic cable and the fluorous sensing phase forms a cladding for the fiber optic cable. A fiber optic cable that includes a cladding also includes an optically transmissive medium optically coupled to the cladding. In some embodiments, the cladding surrounds a cylinder formed of the optically transmissive medium. In operation, as the fluorous sensing phase 2204 detects a target material, such as an analyte, the dielectric constant of the cladding changes and the speed of electromagnetic radiation traveling through the fiber optic cable changes. Thus, detection of a target material by the fluorous sensing phase 2204 results in a change in transmission time for an electromagnetic pulse traveling along the optically transmissive medium 2202. Such a change in transmission time can be used to signal detection of the analyte.

The apparatus 2200 can be used in a method to detect a target material. In some embodiments, the method includes measuring a first transmission time of a first electromagnetic pulse through a transmission medium including a fluorous phase, measuring a second transmission time of a second electromagnetic pulse through the transmission medium including the fluorous phase, and identifying a target material detected by the fluorous phase by observing a difference between the first transmission time and the second transmission time.

In an alternative embodiment, the reduction or increase in the amount of transmitted light due to absorption or fluorescence in the fluorous cladding or at the surface of the fluorous cladding is measured.

Substrate Based Detector

A fluorous phase sensor can be formed on a substrate to produce a substrate based detector. FIG. 23 is a block diagram of an apparatus 2300 including a substrate 2302 including an optically transmissive medium 2304 having a fluorous phase sensor 2306 in accordance with some embodiments. The substrate 2302 is not limited to a particular substrate material. Exemplary materials suitable for use in connection with the fabrication of the substrate 2302 include gallium arsenide, silicon, silicon on sapphire, germanium, and germanium on silicon. Processes suitable for the fabrication of integrated circuits can be used to fabricate the optically transmissive medium 2304. Exemplary technologies suitable for use in forming the optically transmissive medium 2304 on the substrate include complementary metal-oxide semiconductor technologies, gallium-arsenide based technologies, and silicon bipolar technologies. The optically transmissive medium 2304 is not limited to a particular material. Any optically transmissive material is suitable for use in connection with the apparatus 2300. Exemplary optically transmissive materials include glass, crystalline silicon, amorphous silicon, germanium, and gallium arsenide. In some embodiments, the fluorous sensing phase sensor forms a cladding for the optically transmissive medium. In operation, the apparatus 2300 detects a target material by observing a change in transmission time for a pulse traveling along a path defined by the optically transmissive medium 2304. The apparatus 2300 is not limited to detecting a single target material. In some embodiments, a plurality of detectors are formed on the substrate 2304 to detect a plurality of target materials. In yet other embodiments, information provided by the apparatus 2300 can be processed further by substrate processing elements or transmitted off the substrate by wireless communication systems formed on the substrate.

What is claimed is:

1. A device for detecting an analyte present in a fluid, the device comprising a fluorous sensing phase wherein the fluorous sensing phase includes a highly fluorinated solvent or a fluorous polymer phase that is amorphous and has a glass transition temperature below room temperature or a fluorous liquid phase.

2. The device of claim 1 wherein the fluorous sensing phase comprises an anion exchanger.

3. The device of claim 2 further comprising in the fluorous sensing phase a salt of a fluorous ion that is soluble in the fluorous sensing phase.

4. The device of claim 1 wherein the fluorous sensing phase comprises a perfluoropolymer.

5. The device of claim 1 wherein the fluorous sensing phase comprises a linear perfluorocarbon, a branched perfluorocarbon, a mono- or polycyclic perfluorocarbon, a linear or branched perfluoropolyether, a perfluoro(trialkylamine), a perfluoropolyamine, a perfluoro(tetraalkylsilane), or a compound with multiple silicon atoms, or a mixture thereof.

6. A device for detecting an analyte present in a fluid, the device comprising a fluorous sensing phase wherein the fluorous sensing phase comprises perfluoroperhydrophenanthrene.

7. The device of claim 1 which comprises a membrane comprising the fluorous sensing phase.

8. A device for detecting an analyte present in a fluid, the device comprising a porous inert support membrane, wherein a fluorous sensing phase is located within the pores of the support membrane.

9. The device of claim 1 wherein the fluorous sensing phase further comprises a fluorous plasticizer.

10. The device of claim 9 wherein the fluorous plasticizer is a linear perfluorocarbon, a branched perfluorocarbon, a mono- or polycyclic perfluorocarbon, a linear or branched perfluoropolyether, a perfluoro(trialkylamine), a perfluoropolyamine, a perfluoro(tetraalkylsilane), or a compound with multiple silicon atoms, or a mixture thereof.

11. The device of claim 9 wherein the fluorous plasticizer is perfluorooctane, perfluorononane, perfluoro(2-methyloctane), perfluorodecaline, $CF_3CF_2CF_2(OCF_2CF_2CF_2)_m OCF_2CF_3$, $CF_3CF_2CF_2(OCF(CF_3)CF_2)_m OCHFCF_3$, perfluorotripentylamine, perfluorotrihexylamine, $CF_3CF_2(N(CF_3)CF_2CF_2)_m CF_2CF_3$, perfluorotetrapentylsilane, perfluorotetrahexylsilane, or $CF_3CF_2(Si(CF_3)_2CF_2CF_2)_m CF_2CF_3$, or a mixture thereof.

12. The device of claim 1 wherein the fluorous sensing phase further comprises a mixture of a fluorous plasticizer and a highly fluorinated polymer.

13. The device of claim 1 wherein the analyte binds to the fluorous sensing phase.

14. A device for detecting an analyte present in a fluid, the device comprising a fluorous sensing phase wherein the fluorous sensing phase further comprises a fluorophilic analyte-binding receptor molecule or an analyte-binding receptor group covalently attached to a perfluoropolymer.

15. The device of claim 14 wherein the analyte is charged.

16. The device of claim 14 wherein the analyte is an inorganic cation or anion.

17. The device of claim 14 wherein the analyte is a proton, a potassium ion, a sodium ion, a calcium ion, a magnesium ion, a chloride ion, a phosphate, a sulfate, a protonated creatinine, or a carbonate.

18. The device of claim 14 wherein the fluorous receptor molecule is a fluorophilic amine.

19. A device for detecting an analyte present in a fluid, the device comprising a fluorous sensing phase, the fluorous sensing phase further comprising a fluorophilic analyte-binding receptor molecule or an analyte-binding receptor group covalently attached to a perfluoropolymer, wherein the fluorous receptor molecule is tris(perfluorooctylpropyl)amine.

20. The device of claim 1 wherein the fluorous sensing phase further comprises a salt of a fluorophilic ion.

21. The device of claim 20 wherein the salt comprises a fluorophilic cation.

22. The device of claim 21 wherein the fluorous cation has the formula $PR_1R_2R_3R_4^+$, or $NR_1R_2R_3R_4^+$, wherein each $R_1$, $R_2$, $R_3$, and $R_4$ is independently a fluorinated group selected to provide the fluorophilic cation.

23. A device for detecting an analyte present in a fluid, the device comprising a fluorous sensing phase, the fluorous sensing phase further comprising a salt of a fluorophilic ion, wherein the salt comprises a fluorophilic cation and the fluorophilic cation is a tris(3,5-bis(1H,1H,2H,2H,3H,3H-perfluoroundecyl)phenyl)methyl)phosphonium cation.

24. The device of claim 20 wherein the salt comprises a fluorophilic anion.

25. A device for detecting an analyte present in a fluid, the device comprising a fluorous sensing phase wherein the fluorous sensing phase further comprises a salt of a fluorophilic ion and the salt comprises a fluorophilic anion and the fluorophilic anion is tetrakis(3,5-bis(hexafluoro-2-methoxy-2-propyl)phenyl)borate, tetrakis-(3,5-bis-(trifluoromethyl)

phenyl)borate, tetrakis[3,5-bis(perfluorohexyl)phenyl]borate, tetrakis[3,5-bis(perfluorooctyl)phenyl]borate, tetrakis[3,5-bis(perfluorodecyl)-phenyl]borate, or tetrakis (pentafluorophenyl)borate.

26. The device of claim 1 fabricated for optical detection.

27. A method for detecting an analyte in a fluid, the method comprising:
contacting the fluid with a device comprising a fluorous sensing phase into which the analyte enters selectively in comparison with other components of the fluid wherein the fluorous sensing phase includes a fluorous polymer phase that is amorphous and has a glass transition temperature below room temperature; and
detecting the presence of the analyte in the fluid.

28. The method of claim 27 wherein the fluid is a biological fluid.

29. A method for detecting an analyte in a fluid, the method comprising:
contacting the fluid with a device comprising a fluorous sensing phase into which the analyte enters selectively in comparison with other components of the fluid; and
detecting the presence of the analyte in the fluid wherein the fluid is a biological fluid and the biological fluid is blood, a blood product, urine, cerebrospinal fluid, stomach fluid, or saliva.

30. The method of claim 27 wherein the fluid is obtained from an environmental sample.

31. The method of claim 30 wherein environmental sample is an air, water or soil sample.

32. The method of claim 27 wherein the analyte is a charged species, and the detection is potentiometric or amperometric.

33. The method of claim 27 wherein the analyte is a charged or a neutral species, and the detection is optical.

34. An apparatus comprising:
a heart assist unit; and
a sensor to receive a fluid and provide a signal to the heart assist unit, the sensor including a fluorous sensing phase.

35. The apparatus of claim 34, wherein the heart assist unit is implanted in a mammal.

36. The apparatus of claim 35, wherein the mammal is a human.

37. An apparatus comprising:
a food processing unit; and
a sensor to receive a food stream having an analyte and to sense the analyte and generate a signal to control the food processing unit, the sensor including a fluorous sensing phase into which the analyte enters selectively in comparison with other components of the food stream.

38. The apparatus of claim 37, wherein the food processing unit is configured to process a beverage.

39. The apparatus of claim 38, wherein the food processing unit is configured to process cheese.

40. An apparatus, comprising:
an optically transmissive medium including a fluorous sensing phase.

41. The apparatus of claim 40, wherein the optically transmissive medium includes a cladding that includes the fluorous sensing phase.

42. The apparatus of claim 40, wherein the optically transmissive medium includes a fiber optic cable.

43. A method, comprising:
measuring a first transmission time of a first electromagnetic pulse through a transmission medium including a fluorous phase;
measuring a second transmission time of a second electromagnetic pulse through the transmission medium including the fluorous phase; and
identifying a target material detected by the fluorous phase by observing a difference between the first transmission time and the second transmission time.

44. An apparatus, comprising:
a substrate including an optically transmissive medium having a fluorous phase sensor wherein the substrate includes a gallium arsenide substrate.

45. An apparatus, comprising:
a substrate including an optically transmissive medium having a fluorous phase sensor wherein the substrate includes a gallium arsenide substrate and the fluorous phase sensor forms a cladding for the optically transmissive medium.

46. An electrochemical sensor with a membrane comprising a copolymer of tetrafluoroethylene and 2,2-bis(trifluoromethyl)-4,5-difluoro-1,3-dioxole, and a plasticizer wherein the plasticizer is a fluorous plasticizer.

47. A device for detecting an analyte present in a fluid, the device comprising a fluorous sensing phase wherein the fluorous sensing phase includes a highly fluorinated solvent.

48. A device for detecting an analyte present in a fluid, the device comprising a fluorous sensing phase wherein the fluorous sensing phase includes a fluorous polymer phase that is amorphous and has a glass transition temperature below room temperature.

49. A device for detecting an analyte present in a fluid, the device comprising a fluorous sensing phase wherein the fluorous sensing phase includes a fluorous liquid phase.

* * * * *

UNITED STATES PATENT AND TRADEMARK OFFICE
CERTIFICATE OF CORRECTION

PATENT NO. : 8,765,060 B2
APPLICATION NO. : 11/915551
DATED : July 1, 2014
INVENTOR(S) : Buhlmann et al.

It is certified that error appears in the above-identified patent and that said Letters Patent is hereby corrected as shown below:

In the Specification

In Column 1, Lines 11-18 under the Statement Regarding Federally Sponsored Research or Development:

Replace:

>   Work relating to this document was supported in part by grants from the National Science Foundation (CTS-0428046) and the National Institutes of Health (1RO1EB005225-01). The United States government may have certain rights in the subject matter of the invention.

With the following revised paragraph:

This invention was made with government support under CTS-0428046 awarded by the National Science Foundation and 1RO1-EB005225-01 awarded by the National Institutes of Health. The government has certain rights in the invention.

Signed and Sealed this
Twelfth Day of May, 2015

Michelle K. Lee
*Director of the United States Patent and Trademark Office*